United States Patent
Shankar et al.

(10) Patent No.: US 8,058,332 B2
(45) Date of Patent: Nov. 15, 2011

(54) PHOSPHORUS-SULFUR FR ADDITIVES AND POLYMER SYSTEMS CONTAINING SAME

(75) Inventors: Ravi B. Shankar, Midland, MI (US); David R. Wilson, Midland, MI (US); William J. Kruper, Sanford, MI (US); Bruce A. King, Midland, MI (US); Michelle L. Hudack, Midland, MI (US); Chun Wang, Midland, MI (US); Ted A. Morgan, Midland, MI (US); Inken Beulich, Buehl (DE); Daniel J. Murray, Midland, MI (US); William Gerald Stobby, Midland, MI (US); Mark W. Beach, Midland, MI (US); Ing Feng Hu, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 12/906,203

(22) Filed: Oct. 18, 2010

(65) Prior Publication Data

US 2011/0034573 A1   Feb. 10, 2011

Related U.S. Application Data

(63) Continuation of application No. 12/004,345, filed on Dec. 20, 2007, now abandoned.

(60) Provisional application No. 60/876,787, filed on Dec. 21, 2006.

(51) Int. Cl.
*C07F 9/6574* (2006.01)
*C07F 9/02* (2006.01)
*C08K 5/49* (2006.01)
*C08J 9/32* (2006.01)

(52) U.S. Cl. ............ 524/119; 524/117; 568/12; 521/79

(58) Field of Classification Search .................. 524/119, 524/117; 568/12; 521/79
See application file for complete search history.

(56) References Cited

U.S. PATENT DOCUMENTS

| | | |
|---|---|---|
| 3,131,207 A | 4/1964 | Ratz |
| 3,341,624 A | 9/1967 | Sherr |
| 3,511,857 A | 5/1970 | Baranauckas |
| 3,547,842 A | 12/1970 | Bright |
| 3,801,677 A | 4/1974 | Baranauckas |
| 3,994,996 A | 11/1976 | Franko-Filipasic |
| 4,049,617 A | 9/1977 | Albright |
| 4,070,336 A * | 1/1978 | Birum ............ 524/118 |
| 4,086,205 A | 4/1978 | Birum |
| 4,160,795 A | 7/1979 | Albright |
| 4,255,324 A | 3/1981 | Granzow |
| 4,268,459 A | 5/1981 | Hoffman |
| 4,593,058 A | 6/1986 | Talley |
| 4,645,787 A | 2/1987 | Talley |
| 5,002,702 A | 3/1991 | Wolf |
| 5,750,601 A | 5/1998 | Staendeke |
| 2009/0149561 A1 * | 6/2009 | Worku et al. ............ 521/79 |

FOREIGN PATENT DOCUMENTS

| | | |
|---|---|---|
| EP | 207380 A | 6/1986 |
| GB | 1532392 A | 11/1978 |
| GB | 2206590 A | 1/1989 |
| JP | 2004-018475 A | 1/2004 |

OTHER PUBLICATIONS

Edmunson, "Cyclic Organophosphorus Compounds-III, Some Stericaly Hindered Pyrophosphates", Tetrahedron 1965, pp. 2379-2387.*
Edmunson, "Cyclic Organophosphorus Compounds-III, Sterically Hindered Pyrophosphates", Tetrahedron 1965, pp. 2379-2387.

* cited by examiner

*Primary Examiner* — William Cheung
(74) *Attorney, Agent, or Firm* — Gary C. Cohn PLLC

(57) ABSTRACT

Phosphorus-sulfur compounds have flame retardant activity in organic polymer systems. The phosphorus-sulfur compounds can be represented by the structure:

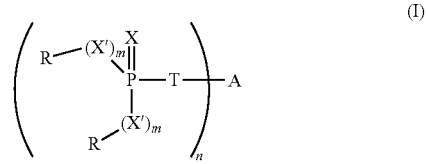

wherein X is oxygen or sulfur, T is a covalent bond, oxygen, sulfur or nitrogen, provided that at least one of X and T is sulfur, each X' is independently oxygen or sulfur, each m is independently zero or 1 when X' is oxygen and zero, 1 or 2 when X' is sulfur, n is at least 1 and preferably at least 2, each R is independently an unsubstituted or inertly substituted hydrocarbyl group or the R groups together form an unsubstituted or inertly substituted divalent organic group and A is an organic linking group.

13 Claims, No Drawings

PHOSPHORUS-SULFUR FR ADDITIVES AND POLYMER SYSTEMS CONTAINING SAME

CROSS-REFERENCE TO RELATED APPLICATION

This application is a continuation of application Ser. No. 12/004,345, filed 20 Dec. 2007, now abandoned and claims priority from U.S. Provisional Patent Application No. 60/876,787, filed 21 Dec. 2006.

BACKGROUND OF THE INVENTION

The present invention relates to flame retardant additives for organic polymers, and in particular phosphorus-sulfur flame suppressant additives.

Flame suppressant additives are commonly added to polymer products used in construction, automotive, electronic, electrical laminate, wire and cable, textile and other applications. FR additives increase the limiting oxygen index (LOI) of polymer systems, allowing articles made from those polymer systems to pass standard fire tests. Various low molecular weight (<~1500 g/mol) brominated compounds are used as FR additives for organic polymers. Many of these, such as hexabromocyclododecane and polybrominated diphenylethers, are under regulatory and public pressure that may lead to restrictions on their use, and there is an incentive to find a replacement for them.

Various phosphorus compounds have been used as FR additives. These include organic phosphates, phosphonates and phosphoramides, some of which are described in U.S. Pat. Nos. 4,070,336 and 4,086,205, as well as in "The Chemistry and Use of Flame Retardants", J. W. Lyons, Chapter 2: *Chemistry of Fire Retardants Based on Phosphorous* p. 29-74 (1987). Another commercially available FR additive is 2,2'-oxybis[5,5-dimethyl-1,3,2-dioxaphosphorinane 2,2'-disulfide], which has the structure:

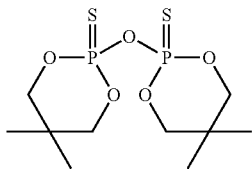

These compounds tend to provide moderate ignition resistance, and are generally not as effective as hexabromocyclododecane or other brominated FR additives.

It is desirable to provide an alternative FR additive for organic polymers, and for foamed polymers in particular. The FR additive should be capable of raising the LOI of the polymer system when incorporated into the polymer at reasonably low levels. Similarly, the FR additive should be capable of conferring good fire extinguishing properties to the polymer system, again when present at reasonably small levels. Because in many cases the FR additive is most conveniently added to a melt of the organic polymer, or else (or in addition) is present in subsequent melt processing operations, the FR additive should be thermally stable at the temperature of the molten polymer. This is typically in the range of 150° C. or higher, and is often above 220° C. It is preferable that the FR additive has low toxicity.

SUMMARY OF THE INVENTION

The present invention is in one aspect a polymer composition comprising a combustible polymer having mixed therein an effective amount of a phosphorus-sulfur additive represented by the structure I:

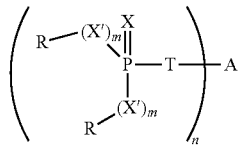

wherein X is oxygen or sulfur, T is a covalent bond, oxygen, sulfur or —$NR^4$—, wherein $R^4$ is hydrogen, alkyl, inertly substituted alkyl or a $P(X)[(X)'_m R]_2$ group, provided that at least one of X and T is sulfur, each X' is independently oxygen or sulfur, each m is independently zero or 1 when X' is oxygen and zero, 1 or 2 when X' is sulfur, n is at least 1 and preferably at least 2, each R is independently an unsubstituted or inertly substituted hydrocarbyl group or the R groups together form an unsubstituted or inertly substituted divalent organic group and A is an organic linking group.

Compounds according to structure (I) often exhibit a highly useful and surprising combination of properties, including in many cases a very low mammalian toxicity and excellent hydrolytic and thermal stability. Their thermal stability permits them to be incorporated into high temperature polymer formulation and processing operations. Unexpectedly, many of these materials have been found to offer outstanding flame retardancy performance when formulated in a variety of polymers and polymer foam structures, especially in poly(vinyl aromatic) types of foam.

In some embodiments, the phosphorus-sulfur additive is one which is represented by the structure II or III:

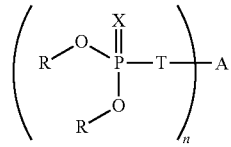

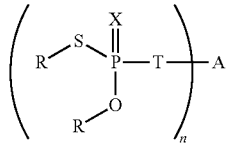

wherein R, X, T, A and n are as described before, again provided that at least one of X and T is sulfur.

In other embodiments, the phosphorus-sulfur additive is one which is represented by the structure IV:

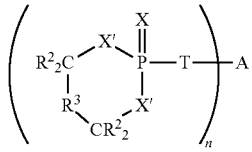

wherein X, X', T, n and A are as defined before, each $R^2$ is independently hydrogen, alkyl or inertly substituted alkyl, and $R^3$ is a covalent bond or a divalent linking group. In structure IV, each $R^2$ is preferably hydrogen, and $R^3$ is preferably an alkylene diradical having no hydrogens on the carbon atom(s) bonded directly to the adjacent $(R^2)_2C$ groups. $R^3$ is more preferably (dialkyl)methylene and most preferably (dimethyl)methylene.

In still other embodiments, the phosphorus-sulfur additive is represented by structure V:

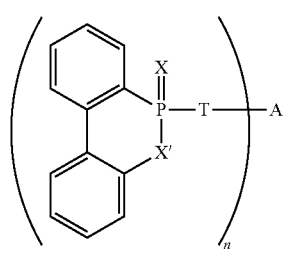

(V)

wherein X, X', T, A and n are as before.

In other respects, this invention is certain phosphorus-sulfur compounds. In some embodiments, the phosphorus-sulfur compound is one represented by structure III. In other embodiments, the phosphorus-sulfur compound is one represented by structure IV or by structure V. In still other embodiments, the phosphorus-sulfur compound is represented by structures I or II, wherein T is oxygen, sulfur or —$NR^4$—, wherein $R^4$ is hydrogen, alkyl or inertly substituted alkyl and A is (1) an organic polymer;
(2) an organic group bonded to the -T- linkage through a benzylic carbon, including organic groups represented by structure VI,

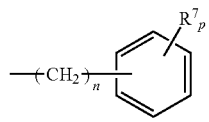

(VI)

wherein $R^7$ is H, hydrocarbyl or an inert substituent and p is 6-n;
(3) an organic group bonded to the -T- linkage through an acrylic or methacrylic group, such as is represented by structure VI

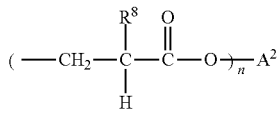

(VII)

wherein $R^8$ is —$CH_3$ or —H, and $A^2$ is an organic linking group;
(4) a residue of an ester of a diol or diacid (such as a maleic acid ester or fumaric acid ester) having non-aromatic carbon-carbon unsaturation, after addition of a phosphorus-sulfur group to the carbon-carbon double bond of the ester;
(5) a residue of a fatty acid or ester thereof (including a fatty acid triglyceride), wherein the fatty acid has at least one carbon-carbon unsaturation site, after addition of a phosphorus-sulfur group to such carbon-carbon unsaturation site, or
(6) an aromatic group bonded to the -T- linkage through an aromatic carbon atom.

DETAILED DESCRIPTION OF THE INVENTION

The phosphorus-sulfur additive is characterized in having at least one phosphorus-sulfur group which contains a phosphorus atom bonded to at least two and preferably at least three sulfur, oxygen or nitrogen atoms, provided that at least one of those atoms is a sulfur atom. The group may contain a single sulfur atom, including moieties of the following types (structure VIII):

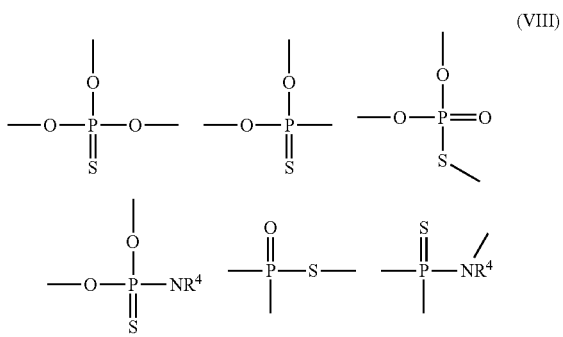

(VIII)

The phosphorus-sulfur group may contain two sulfur atoms bonded to the phosphorus atom, including moieties of the following types (structures IX):

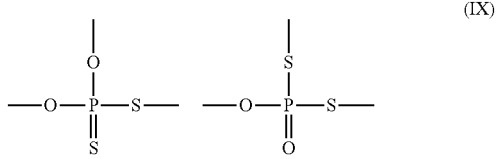

(IX)

The phosphorus-sulfur group may contain 3 or 4 sulfur atoms bonded to the phosphorus atom, as shown in structure X:

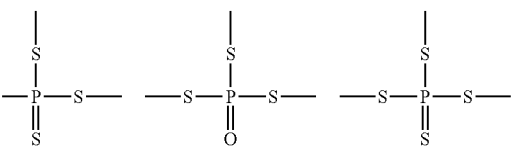

(X)

In addition, the phosphorus-sulfur group includes moieties in which the phosphorus atom is bonded directly to a carbon atom (of an A group and/or an R group, as described before) such as is shown in structure XI:

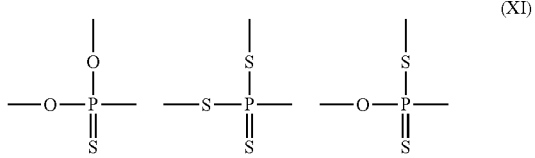

(XI)

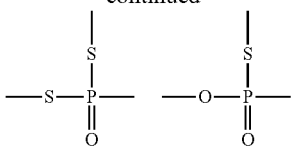

Thus, certain useful types of suitable nonhalogenated phosphorus-sulfur additives can be represented by structure II and III:

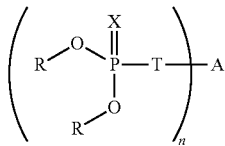
(II)

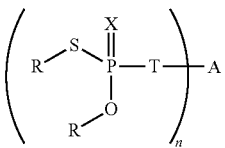
(III)

wherein R, X, T, A and n are as described before, and at least one of X and T is sulfur. In structures II and III, T is preferably oxygen or sulfur, most preferably sulfur. X is preferably sulfur and n is preferably at least 2.

In structures I, II or III, the R groups may be, for example, unsubstituted or inertly substituted aliphatic, cycloaliphatic or aromatic groups.

In this application, an "inert" substituent is one that does not undesirably interfere with the flame retardant properties of the additive. A compound containing an inert substituent is said to be "inertly substituted". The inert substituent may be, for example, an oxygen-containing group such as an ether, ester, carbonyl, hydroxyl, carboxylic acid or oxirane group, and the like. The inert substituent may be a nitrogen-containing group such as a primary, secondary or tertiary amine group, an imine group, an amide group or a nitro group. The inert substituent may contain other hetero atoms such as sulfur, phosphorus, silicon (such as silane or siloxane groups) and the like. The inert substituent is preferably not a halogen and does not contain a halogen.

A hydrocarbyl group, for purposes of this invention, is a group that, except for inert substituents, contains only hydrogen and carbon atoms. A hydrocarbyl group may be aliphatic, alicyclic, aromatic or some combination of two or more of those types.

The R groups in structures I, II or III are preferably unsubstituted or inertly substituted lower alkyl, such as methyl, ethyl, n-propyl, isopropyl, n-butyl, isobutyl, t-butyl, sec-butyl and the like. More preferably, the two R groups together form a divalent organic radical that completes a ring structure with the $—(X')_m—P—(X')_m—$, $—O—P—O—$ or $—S—P—O—$ linkage, respectively, as shown for example in structure IV above. An especially preferred phosphorus-sulfur additive is a compound represented by structure XII:

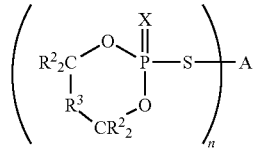
(XII)

wherein X, n $R^2$, $R^3$ and A are as described before (X preferably being sulfur). In structures IV and XII, the $R^2$ groups are preferably hydrogen or lower alkyl and more preferably hydrogen. $R^3$ is preferably a straight-chain or branched hydrocarbyl group, —O—, or a covalent bond. More preferred $R^3$ groups are hydrocarbyl groups that are gem-disubstituted on the carbon atom or carbon atoms that are bonded directly to the $R^2C$ groups. The $R^3$ group is most preferably dialkyl-substituted methylene, as is the case when the $R^3$ group is (dimethyl)methylene.

An especially preferred type of phosphorus-sulfur additive is represented by the structure XIII:

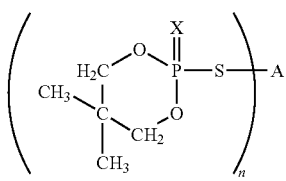
(XIII)

where X, n and A are as before. X is preferably sulfur.

Another type of phosphorus-sulfur additive is represented by the structure V:

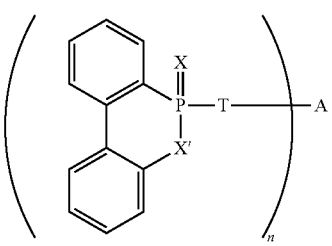
(V)

in which X', T and X are each preferably sulfur, and A and n are as defined before.

The A group in structures I, II, III, IV, V, XII and XIII is an organic linking group. The organic linking group may have a wide variety of possible structures. An organic linking group is covalently bonded to the -T- linkage (in structures I-V and XIII) or the —S— atom (in structure XII). The -T- or —S— linkage may be bonded to a carbon atom or a heteroatom on the organic linking group A, but is preferably bonded to a carbon atom. That carbon atom is preferably a primary or secondary carbon atom (i.e, is bonded to 1 or 2 other carbon atoms), but is less preferably a tertiary carbon atom (i.e., one bonded to three other carbon atoms).

One type of organic linking group A is an unsubstituted or inertly substituted hydrocarbyl group. The organic linking group A may contain any number of carbon atoms, although it is preferred that the molecular weight per phosphorus-sulfur group does not exceed about 2000 daltons, more preferably does not exceed about 1500 daltons, and especially is below 1000 daltons. The phosphorus-sulfur additive may contain from 5 to 50% or more sulfur by weight, and when A is an organic polymer, the phosphorus-sulfur FR additive preferably contains from 5 to 30% by weight sulfur. The organic linking group A may be aliphatic (linear or branched), alicyclic, aromatic, or some combination of these. The valence of the organic linking group A is equal to n. In each of structures I-V, XII and XIII, n is preferably at least 2.

An organic linking group A may be a linear or branched, substituted or unsubstituted alkylene radical having a valence equal to n. Any number of carbon atoms may be contained in the alkylene radical. An example of an additive having an A group which is a substituted (in this case with ether groups) alkylene radical is represented by structure XIV:

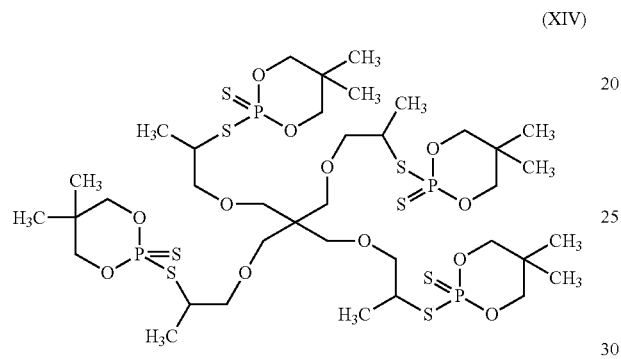
(XIV)

An organic linking group A may be an unsaturated hydrocarbyl group. In such a case, it is preferred that the A group is bonded to the -T- linkage of each phosphorus-sulfur group through an allylic or benzylic carbon atom. Examples of compounds in which the phosphorus-sulfur group is bonded to an allylic carbon are represented by structures XV and XVI, where X, R, $R^2$ and $R^3$ are as defined before.

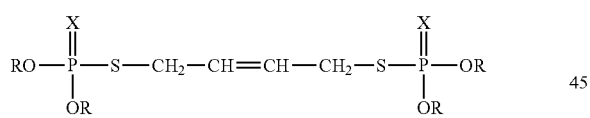
(XV)

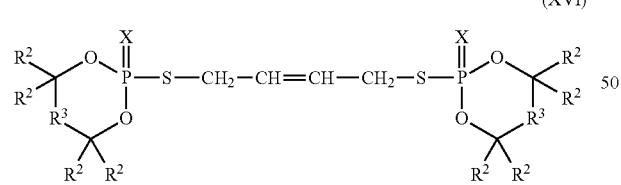
(XVI)

In structures XV and XVI, the $R^2$ groups are preferably hydrogen or lower alkyl and more preferably hydrogen, and the $R^3$ groups are hydrocarbyl groups that are gem-disubstituted on the carbon atom or carbon atoms that are bonded directly to the $R^2C$ groups, preferably dialkyl-substituted methylene, especially (dimethyl)methylene.

Another type of linking group A for structures I-V, XII and XIII, which is bonded to the -T- or —S— linkage (as the case may be) through a benzylic carbon atom, is represented by structure VI above. Specific examples of phosphorus-sulfur additives containing this type of A group are shown in structures XVII-XXIII, as follow:

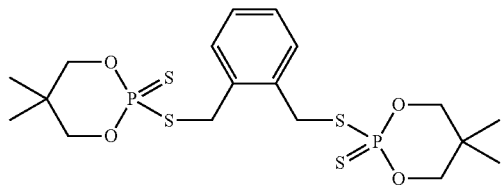
(XVII)

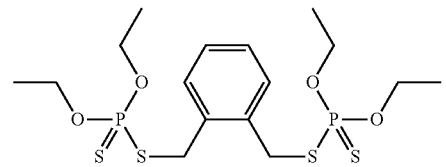
(XVIII)

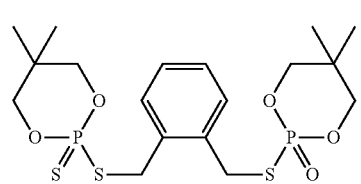
(XIX)

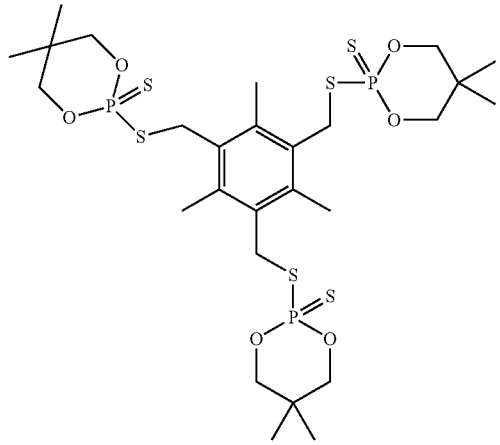
(XX)

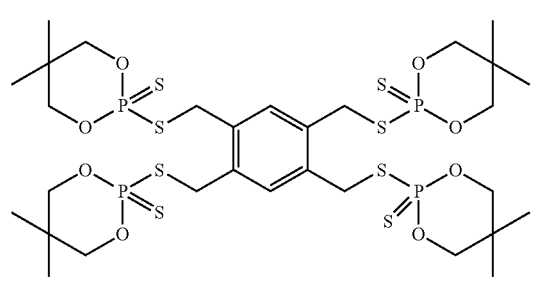
(XXI)

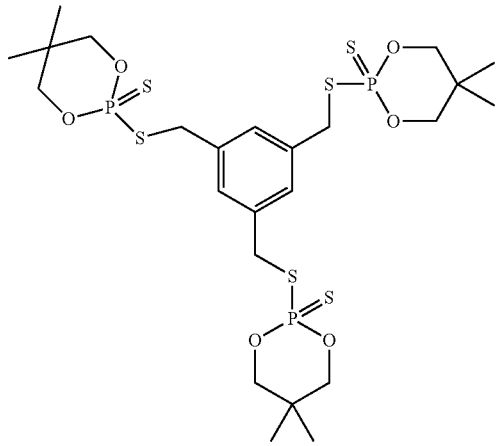

(XXII)

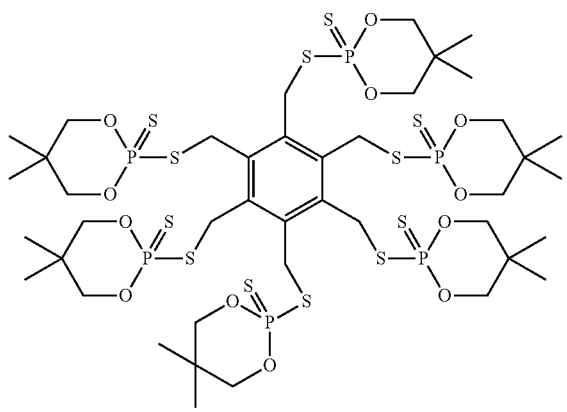

(XXIII)

It is also possible for the phosphorus-sulfur groups to be bonded directly to an aromatic ring of an A group.

Another type of organic linking group A in structures I-V, XII and XIII is a residue of a compound having acrylate or methacrylate groups, after addition of the phosphorus-sulfur starting material across the carbon-carbon double bond of the acrylate or methacrylate groups. In such a case, the linking group A can be represented by structure VII above. A specific type of phosphorus-sulfur FR additive of this type is a reaction product of an acrylate ester of a polyol compound with 5,5-dimethyl-2-thioxo-[1,3,2]dioxaphosphorinane-2-thiol.

Yet another type of organic linking group A in structures I-V, XII and XIII is a residue of an unsaturated fatty acid or an ester of such a fatty acid (including, notably, a triglyceride of such a fatty acid, in which at least a portion of the constituent fatty acids contains carbon-carbon unsaturation), the reside being what remains after addition of the phosphorus-sulfur starting material across a carbon-carbon double bond of the fatty acid or ester. Vegetable oils such as soy, canola, olive and corn oil are examples of such triglycerides.

Still another type of organic linking group A in structures I-V, XII and XIII is a residue, after addition of the phosphorus-sulfur group across the carbon-carbon double bond, of a maleic or fumaric ester or ester made from another diol or diacid having non-aromatic carbon-carbon unsaturation. A specific type of phosphorus-sulfur FR additive of this type is a reaction product of a maleic diester with 5,5-dimethyl-2-thioxo-[1,3,2]dioxaphosphorinane-2-thiol.

Other organic linking groups A may contain various heteroatoms, including oxygen, phosphorus, sulfur, nitrogen and the like. An example of a phosphorus and oxygen-containing linking group A is a phosphine moiety represented by structure XXIV:

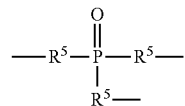

(XXIV)

wherein each $R^5$ is divalent alkyl or inertly substituted divalent alkyl, preferably ethylene or methylene. Among the organic linking groups A that contain heterotoms are heterocyclic compounds that contain a heteroatom in a ring structure. The heterocyclic compounds can be aliphatic or aromatic. Heterocyclic aromatic compounds are of partular interest. An example of such a heterocyclic aromatic compound is a phosphazene or a triazine structure:

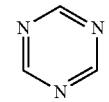

which can be substituted with a phosphorus-sulfur group at any or all ring carbons.

Some phosphorus-sulfur additives in accordance with the invention include those of any of structures I-V, XII or XIII, in which organic linking group A is an organic polymer. Polymer organic linking groups A which are bonded to pendant phosphorus-sulfur groups are preferred embodiments of the invention. A wide range of organic polymers can serve as the linking group A, as long as the organic polymer that is used to form organic linking group A has functional groups that can react to form a bond to the -T- or —S— linkage (as the case may be) of a phosphorus-sulfur group.

A polymer or copolymer that forms the A group may have a weight average molecular weight of from about 500 to 300,000 or more. However, those having lower weight average molecular weights, such as from 1000 to 20,000, especially from 2000 to 10,000, tend to disperse better in many polymers, especially styrene homopolymers and copolymers and may be more efficient at providing flame retardant properties.

One suitable type of organic polymer that can be used to form organic linking group A contains or is modified to contain aliphatic carbon-carbon unsaturation that can react to form a bond to a phosphorus-sulfur group. Examples of organic polymers that contain aliphatic carbon-carbon unsaturation include homopolymers of a conjugated diene such as butadiene, isoprene or cyclopentadiene, or copolymers of two or more conjugated dienes or of at least one conjugated diene and at least one other copolymerizable monomer. Examples of the last type include copolymers of butadiene or isoprene and a vinyl aromatic monomer such as styrene. Another example of an organic polymer that contains aliphatic carbon-carbon unsaturation is a polymer or copolymer of a monomer having two ethylenically unsaturated groups of unequal reactivity, such as allyl acrylate, allyl methacrylate and the like. The more reactive of these groups can be preferentially polymerized to form a polymer having pendant ethylenic unsaturation. Yet another example of an organic polymer having aliphatic carbon-carbon unsaturation is a polyester of an unsaturated aliphatic diacid such as maleic acid or fumaric acid (or the corresponding diesters or anhydrides).

An organic polymer can be modified in various ways to introduce aliphatic carbon-carbon unsaturation, and such modified polymers can be used to form the organic linking group A. A convenient way of introducing such unsaturation is through the reaction of a reactive group on the organic polymer with an unsaturated compound that contains ethylenic unsaturation and a coreactive group that reacts with the reactive group on the organic polymer to form a bond. For example, acrylic, acrylate, methacrylic and methacrylate compounds of various types can react with reactive groups such as hydroxyl, ester, primary or secondary amino and like groups to introduce acrylate or methacrylate functionality to an organic polymer.

Other organic polymers which can be used to form organic linking group A contain other types of reactive sites through which the polymer can bond to the -T- linkage or —S— atom of a phosphorus-sulfur group. Examples of such groups include epoxide groups and halogen (particularly chlorine or bromine) substitution.

A wide variety of epoxy resins can be used to form the organic linking group A. Examples of these include the diglycidyl ethers of polyhydric phenol compounds such as resorcinol, catechol, hydroquinone, bisphenol, bisphenol A, bisphenol AP (1,1-bis(4-hydroxylphenyl)-1-phenyl ethane), bisphenol F, bisphenol K, tetramethylbiphenol, diglycidyl ethers of aliphatic glycols and polyether glycols such as the diglycidyl ethers of $C_{2-24}$ alkylene glycols and poly(ethylene oxide) or poly(propylene oxide) glycols; polyglycidyl ethers of phenol-formaldehyde novolac resins, alkyl substituted phenol-formaldehyde resins (epoxy novalac resins), phenol-hydroxybenzaldehyde resins, cresol-hydroxybenzaldehyde resins, dicyclopentadiene-phenol resins, dicyclopentadiene-substituted phenol resins, and the like.

Organic polymers useful to form organic linking group A, and which are substituted with halogens include, for example, polymers and copolymers of halogenated monomers such as vinyl chloride, vinylidene chloride, vinylbenzyl chloride, and the like. Alternatively, halogen groups can be introduced onto a previously-prepared polymer in a number of ways. It is noted that polymers of vinylbenzyl chloride form phosphorus-sulfur additives in which the phosphorus-sulfur group(s) are bonded to an benzylic carbon atom.

An organic polymer linking group A of particular interest is a residue (after addition of the phosphorus-sulfur group to a carbon-carbon double bond of the polymer) of a polymer or copolymer of a conjugated diene, and especially a polymer or copolymer of butadiene or isoprene with at least one vinyl aromatic monomer such as styrene. The copolymers may be random or block types. Block types of particular interest are diblock copolymers, and triblock copolymers which contain a central polybutadiene block and terminal polystyrene blocks. The diblock copolymers are somewhat preferred over the triblock types for use in forming the organic linking group A, particularly for applications in polyvinyl aromatics such as polystyrene. Prior to introducing the phosphorus-sulfur groups, the copolymer contains at least 10% by weight of polymerized butadiene. Butadiene polymerizes to form two types of repeating units. One type, referred to herein as "1,2-butadiene units", takes the form

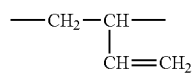

and so introduces pendant unsaturated groups to the polymer. The second type, referred to herein as "1,4-butadiene units", takes the form —$CH_2$—CH=CH—$CH_2$— and introduces unsaturation into the main polymer chain. A butadiene/vinyl aromatic polymer used as the organic liking group A preferably contains at least some 1,2-butadiene units, prior to the addition of the phosphorus-sulfur group. Of the butadiene units in the butadiene/vinyl aromatic polymer, at least 10%, preferably at least 15% and more preferably at least 20% and even more preferably at least 25% are 1,2-butadiene units, prior to addition of the phosphorus-sulfur group. 1,2-butadiene units may constitute at least 50%, at least 55%, at least 60% or at least 70% of the butadiene units in the butadiene/vinyl aromatic copolymer prior to addition of the phosphorus-sulfur group. The proportion of 1,2-butadiene units may be in excess of 85% or even in excess of 90% of the butadiene units in the starting copolymer. Methods for preparing butadiene/vinyl aromatic polymers with controlled 1,2-butadiene content are described by J. F. Henderson and M. Szwarc in *Journal of Polymer Science* (D, Macromolecular Review), Volume 3, page 317 (1968), Y. Tanaka, Y. Takeuchi, M. Kobayashi and H. Tadokoro in *J. Polym. Sci.* A-2, 9, 43-57 (1971), J. Zymonas, E. R. Santee and H. James Harwood in *Macromolecules*, 6, 129-133 (1973), and H. Ashitaka et al., in *J. Polym. Sci., Polym. Chem.*, 21, 1853-1860 (1983).

Polymers of one or more conjugated dienes can be subjected to bromination with N-bromosuccinimide, for example, to give allylically-brominated polymers. Such allylically-brominated polymers can lead to linking groups A wherein the A group is bonded to the -T- or —S— linkage through allylic carbon atoms.

The phosphorus-sulfur additives in most cases can be prepared straightforwardly using simple chemistry. Phosphorus-sulfur starting materials are readily prepared by contacting an alcohol with $P_2S_5$, which is readily available as a lubricating agent and a raw material for biocide manufacture. The alcohol has the structure ROH, where R is as defined in structure I above. The resulting phosphorus-sulfur starting material has the structure XXV, as follows.

wherein X and R are as defined before. Dialcohols of the form HO—C($R^2$)$_2$—$R^3$—C($R^2$)$_2$OH (where $R^2$ and $R^3$ are as defined with regard to structure IV above) can react with $P_2S_5$ to form cyclic phosphorus-sulfur starting materials having the structure XXVI:

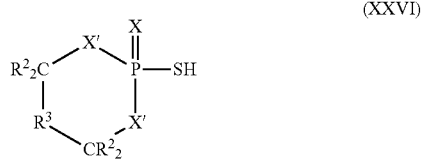

where X, X', $R^2$ and $R^3$ are as defined before. Compounds of this type can be prepared using methods described in Chauhan, H. P. S.; Bhasin, C. P.; Srivastava, G.; Mehrotra, R. C., "Synthesis and characterization of 2-mercapto-2-thioxo-1,3,2-dioxaphospholanes and dioxaphosphorinanes", *Phosphorus and Sulfur and the Related Elements (1983), 15(1), 99-104 and in Edmundson, "Cyclic Organophosphorus Compounds-III, Some Sterically Hindered Pyrophosphates", *Tetrahedron*, 1965, 2379-2387. An especially preferred phosphorus-sulfur starting material is:

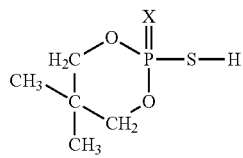

where X is as before, and is preferably sulfur.

The phosphorus-sulfur starting compounds can be formed into the corresponding amine salts by mixing with a primary, secondary or, preferably, tertiary amine compound, and the resulting amine salts can react with an organic halide to form the phosphorus-sulfur flame retardant agent. This sequence of reaction is conveniently done in a solvent for the starting materials and can be done at room temperature, at a slightly reduced temperature, or at some elevated temperature below the decomposition temperature of the starting materials. A temperature of from 10 to 100° C. is suitable. The reaction can be illustrated schematically by the idealized reaction scheme XXVII.

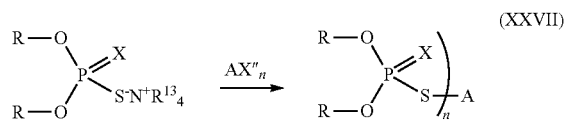

wherein each $R^{13}$ is independently hydrogen, hydrocarbyl or inertly substituted hydrocarbyl, X" is a halogen, preferably chlorine or bromine, and R, n, A and X are as defined before.

The phosphorus-sulfur starting compounds can also be reacted directly with electrophiles such as ortho-dixylyldichloride, 1,4-dibromo-2-butene, without first producing the ammonium salt, as described in Kaboudin, B.; Norouzi, H., *Synthesis*, 2004, 12, 2035-2039.

The reagent $AX''_n$ may be, for example, an alkane or alkene substituted with 1 or more, preferably 2 or more, preferably 2 to 4 halogen atoms, which are most preferably chlorine or bromine. Examples of such substituted alkanes and alkenes include 1,4-butane dichloride, 1,4-butane dibromide, 1,2 ethylene dichloride, 1,2-ethylene dibromide, 1,2-propylene dichloride, 1,2-propylene dibromide, 1,4-dibromo-2-butene, 1,4-dichloro-2-butene, and the like. The reagent $AX''_n$ may instead be an aromatic compound that is substituted with one or more haloalkyl groups, especially bromomethyl or chloromethyl groups and optionally other ring substitutions. Examples of such aromatic compounds include benzyl chloride, o- m- or p-xylyldichloride, o-, m- or p-xylyldibromide, 1,2,4,6-tetra(bromomethyl)benzene, 1,2,4,6-tetra(chloromethyl)benzene, 1,2,3,4,5,6-hexa(bromomethyl)benzene, 1,2, 3,4,5,6-hexa(chloromethyl)benzene, 1,3,5-tris(bromomethyl)-2,4,6-trimethylbenzene, 1,3,5-tris(chloromethyl)-2,4, 6-trimethylbenzene, poly(vinylbenzylchloride), poly(vinyl benzylbromide) and copolymers of poly(vinylbenzylchloride) and/or poly(vinylbenzylchloride) with at least one other copolymerizable monomer, polymers and copolymers of vinyl chloride and vinylidene chloride, and the like.

In another route to producing the phosphorus-sulfur additivess, the phosphorus-sulfur starting material is contacted directly with a compound having one or more aliphatic carbon-carbon double bonds, as shown schematically in reaction sequence XXVIII. The reaction can be conducted in a solvent for the starting materials, and can be performed at any convenient temperature below the decomposition temperature of the starting materials. A temperature of from 0 to 100° C. is suitable. Reaction sequence XXVIII is:

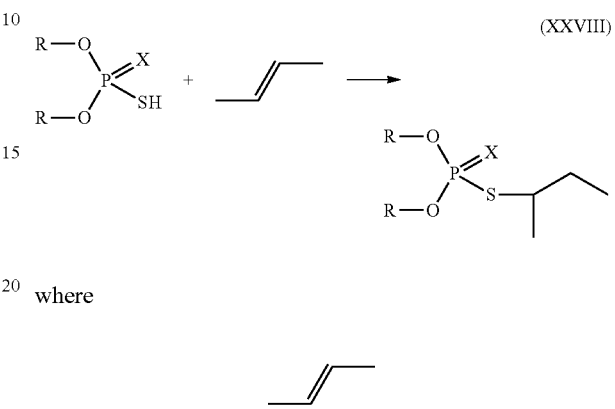

where represents a compound having a carbon-carbon double bond. The carbon-carbon double bond may be of the cis or trans configuration. Reactions of this type are described, for example, in Mehbah et al., Phosphorous, *Sulfur and Silicon and The Related Elements* 1992, 73, 49-56.

The unsaturated compound can contain only one carbon-carbon double bond, or may contain two or more of such double bonds. If multiple double bonds are present, they may or may not be conjugated, but at least one of them is not aromatic in character. The double bonds may be present in a non-aromatic ring structure. Examples of suitable olefin compounds include, for example, ethylene, propylene, 1- or 2-butene, 1- or 2-pentene, higher alpha-olefins such as 1-hexene and 1-octene, butadiene, isoprene, cyclopentene, cyclopentadiene, dicyclopentadiene, 1,5,9-dodecatriene, styrene, divinylbenzene, trivinylbenzene, ethylidene norbornene, norbornene, norbornadiene, vinylcyclohexane, cyclooctadiene, 1,6-octadiene, compounds and adducts containing acrylate and/or methacrylate groups, polymers and copolymers of butadiene and/or isoprene (including block or random copolymers of butadiene with a vinyl aromatic monomer such as styrene), and the like.

The phosphorus-sulfur starting material can be contacted with an oxirane compound, such as an epoxy resin as described before, to produce a phosphorus-sulfur flame retardant compound useful in the invention. In this case, the -T-H group reacts with an epoxy group, opening the epoxide ring and forming an —OH group (corresponding to the oxygen atom of the oxirane ring). This reaction may be performed in a solvent for the starting materials, at a temperature from slightly below room temperature to the decomposition temperature of the starting materials. A temperature of from 10° C. to 100° C. is suitable. This reaction may be catalyzed if desired.

The phosphorus-sulfur additive is useful as a flame retardant additive for a variety of combustible polymers. "Combustible" here simply means that the polymer is capable of being burned. The combustible polymer may be a thermoplastic or thermoset polymer.

Combustible polymers of interest include polyolefins such as polyethylene (including copolymers of ethylene such as ethylene-α-olefin copolymers, polypropylene and the like); polycarbonates and blends of polycarbonates such as blends of a polycarbonate with a polyester, an acrylonitrile-styrene-butadiene resin, a styrene-acrylonitrile resin or polystyrene; polyamides; polyesters; epoxy resins; polyurethanes; polyisocyanurates, and vinyl aromatic polymers (including vinyl aromatic homopolymers, vinyl aromatic copolymers, blends of one or more vinyl aromatic homopolymers and/or vinyl aromatic copolymers with another polymer, such as poly (phenylene oxide) resin and rubber-modified vinyl aromatic polymers); vinyl ester resins; thermoplastic or thermoset vinyl ester resins, as well as other flammable polymers in which the phosphorus-sulfur additive can be dissolved or dispersed.

Polyolefins are polymers of particular interest. The polyolefin polymers are polymers or interpolymers containing repeated units derived by polymerizing an α-olefin. Particularly suitable α-olefins have from 2 to about 20 carbon atoms, preferably from 2 to about 8 carbon atoms, and include ethylene, propylene, 1-butene, 4-methyl-1-pentene, 1-hexene, 1-octene and the like. Preferred α-olefin polymers are homopolymers of ethylene or propylene and interpolymers of ethylene with a $C_3$-$C_8$ α-olefin. The α-olefin polymer may also contain, in polymerized form, one or more other monomers that are interpolymerizable with the α-olefin and which contain an aliphatic or cycloaliphatic group. Such monomers include, for example, vinyl acetate, acrylic acid, methacrylic acid, esters of acrylic or methacrylic acid and acid anhydrides such as maleic anhydride. The α-olefin polymer preferably contains at least 75% by weight, preferably at least 95% by weight, of polymerized α-olefin monomers. More preferably, the α-olefin polymer is an interpolymer polymer of at least 85% by weight polymerized ethylene, and up to 15% by weight of another α-olefin. Particularly suitable α-olefin polymers include low density polyethylene (LDPE), which term is used herein to designate polyethylene homopolymers made in a high pressure, free radical polymerization process. Linear low density polyethylene (LLDPE) and high density polyethylene (HDPE) products are also useful herein. LLDPE polymers having a homogeneous distribution of the comonomer are described, for example, in U.S. Pat. No. 3,645,992 to Elston and U.S. Pat. Nos. 5,026,798 and 5,055,438 to Canich are also useful. Another useful type of α-olefin polymer is a substantially linear olefin polymer as described in U.S. Pat. Nos. 5,272,236 and 5,278,272, incorporated herein by reference. Still another suitable α-olefin polymer is a homopolymer or interpolymer of propylene. An interpolymer of propylene may by an interpolymer of propylene and one or more other monomers such as another α-olefin, vinylacetate, methylacrylate, ethylacrylate, methyl methacrylate, acrylic acid, itaconic acid, maleic acid, and maleic anhydride.

Another combustible polymer of particular interest is a vinyl aromatic polymer. A "vinyl aromatic" polymer is a polymer of an aromatic compound having a polymerizable ethylenically unsaturated group bonded directly to a carbon atom of an aromatic ring. Suitable vinyl aromatic polymers include homopolymers of vinyl aromatic monomers and copolymers thereof with up to 50% by weight of one or more copolymerizable ethylenically unsaturated compounds. The vinyl aromatic polymer or copolymer may be used alone or as a blend with another vinyl aromatic polymer or copolymer and/or with a polymer of a different type (such as, for example, a poly(phenylene oxide) or poly-1,6-(2,6-dimethylphenyl)ether. The vinyl aromatic polymer preferably has a weight average molecular weight of from 100,000 to 350,000, measured using size exclusion chromatography. Suitable vinyl aromatic monomers include unsubstituted materials such as styrene, divinylbenzene and vinyl naphthalene, as well as compounds that are substituted on the ethylenically unsaturated group (such as, for example alpha-methylstyrene), and/or are ring-substituted. Ring-substituted vinyl aromatic monomers include those having halogen, alkoxyl, nitro or unsubstituted or substituted alkyl groups bonded directly to a carbon atom of an aromatic ring. Examples of such ring-substituted vinyl aromatic monomers include 2- or 4-bromostyrene, 2- or 4-chlorostyrene, 2- or 4-methoxystyrene, 2- or 4-nitrostyrene, 2- or 4-methylstyrene, ethylstyrene and 2,4-dimethylstyrene. Suitable copolymerizable monomers include acrylic acid, methacrylic acid, ethacrylic acid, maleic acid, itaconic acid, acrylonitrile, maleic anhydride, methyl acrylate, ethyl acrylate, butyl acrylate, propyl acrylate, methyl methacrylate, vinyl acetate, vinyl alcohol, certain amides, and butadiene Foamed polymers of any of these types are of interest.

Thermoplastic and thermoset vinyl ester resins as described, for example, in "Vinyl Ester Polymers", Encyclopedia of Polymer Science and Engineering, Mark et al., ed., Vol. 17, pp. 393-445 (1989), are also of particular interest.

A combustible polymer of particular interest is a polymer or copolymer of a vinyl aromatic monomer, such as a styrene polymer or copolymer as described before, a styrene-acrylonitrile polymer (SAN), a rubber-modified polystyrene (such as high impact polystyrene), or a styrene-acrylonitrile-butadiene (ABS) resin. Polystyrene is an especially preferred combustible polymer.

Another combustible polymer of particular interest is a random, block or graft copolymer of butadiene and at least one vinyl aromatic monomer. Among these, block copolymers are preferred, and diblock or triblock copolymers of butadiene and styrene are especially preferred.

The combustible polymer may be (either prior to or following the incorporation of the phosphorus-sulfur additive) in the form of any type of fabricated article, including without limitation a film, sheet, fiber, foam or a molded article.

Foamed combustible polymers of any of the foregoing types are of particular interest, as they find applications in vehicles and construction in which fire characteristics are of concern. A foamed combustible polymer suitably has a foam density of from about 0.5 to about 30 pounds per cubic foot (pcf) (8-480 kg/m$^3$), especially from about 0.8 to about 10 pcf (12.8 to 160 kg/m$^3$) and most preferably from about 1 to about 4 pcf (16 to 64 kg/m$^3$). A foamed combustible polymer can be made via any suitable process, including extrusion processes, reactive foaming processes and expanded bead processes. The phosphorus-sulfur additives of the inventions often are suitable for manufacturing extruded polymer foams, because the compounds in many cases have sufficient thermal stability, as indicated by the 5% weight loss temperature test described below, to be introduced into the foam extrusion process by which the foam is made. Extruded polystyrene foam and expanded polystyrene bead foam are especially preferred combustible polymers.

Enough of the phosphorus-sulfur additive is used to improve the performance of the combustible polymer in one or more standard fire tests. One such test is a limiting oxygen index (LOI) test, which evaluates the minimum oxygen content in the atmosphere that is needed to support combustion of the polymer. LOI is conveniently determined in accordance with ASTM D2863. The combustible polymer containing the phosphorus-sulfur compound preferably has an LOI at least 2%, more preferably at least 3%, higher than that of the combustible polymer alone. When the combustible polymer is a polystyrene, the LOI of the polystyrene-FR additive mixture is at least 20%, more preferably at least 23% and even more preferably at least 25%. Another fire test is a time-to-extinguish measurement, known as FP-7, which is determined according to the method described by A. R. Ingram in *J. Appl. Poly. Sci.* 1964, 8, 2485-2495. This test measures the time required for flames to become extinguished when a polymer sample is exposed to an igniting flame under specified conditions, and the ignition source is then removed. In general, FP-7 values should be as low as possible. For a polystyrene polymer containing the FR additive described herein, an FP-7 value of less than 10 seconds, preferably less than 5 seconds, even more preferably less than 2 seconds, is desired. Generally, these results can be obtained when the phosphorus-sulfur FR additive constitutes from 1 to about 15, preferably from 1 to about 6 weight percent of the compounded combustible polymer.

It is convenient in many cases to blend the phosphorus-sulfur FR additive into the molten combustible polymer, either prior to or during another melt processing operation (such as extrusion, foaming, molding, etc.). Because of this, the phosphorus-sulfur FR additive is preferably thermally stable at the temperature at which the molten polymer is processed. This temperature is, for many combustible polymers, typically above 150° C., and for many combustible polymers of particular interest (such as polystyrene) is above 200° C., or even 220° C. or higher.

A useful indicator of thermal stability is a 5% weight loss temperature, which is measured by thermogravimetric analysis as follows: ~10 milligrams of the phosphorus-sulfur FR additive is analyzed using a TA Instruments model Hi-Res TGA 2950 or equivalent device, with a 60 milliliters per minute (mL/min) flow of gaseous nitrogen and a heating rate of 10° C./min over a range of from room temperature (nominally 25° C.) to 600° C. The mass lost by the sample is monitored during the heating step, and the temperature at which the sample has lost 5% of its initial weight is designated the 5% weight loss temperature (5% WLT). This method provides a temperature at which a sample undergoes a cumulative weight loss of 5 wt %, based on initial sample weight. The phosphorus-sulfur additive preferably exhibits a 5% WLT of at least the temperature at which the combustible polymer is to be melt-processed (to blend it with the phosphorus-sulfur FR additive or to process the blend into an article such as a foam, extruded part, molded part, or the like). When it is to be used in a melt-processing operation with a combustible polymer, the phosphorus-sulfur FR additive should have a 5% WLT of at least 150° C. The 5% WLT is preferably at least 200° C., more preferably at least 225° C., even more preferably at least 240° C., and still more preferably at least 250° C., particularly when the combustible polymer is polystyrene.

It is also possible to blend the phosphorus-sulfur additive with a combustible polymer using other methods, such as mixing it into a solution of the combustible polymer, by adding it into a suspension polymerization or emulsion polymerization process, or in other ways. Thermal stability of the phosphorus-sulfur additive is less important if the combustible polymer is not melt-processed in the presence of the phosphorus-sulfur additive, as the phosphorus-sulfur additive in such cases is generally not exposed to such high temperatures during the processing.

Polymer blends in accordance with the invention may include other additives such as other flame retardant additives, thermal stabilizers, ultraviolet light stabilizers, nucleating agents, antioxidants, foaming agents, fillers, crosslinking and/or grafting agents, acid scavengers and coloring agents.

Polymer blends containing phosphorus-sulfur FR additives in accordance with the invention may be melt or solution processed to form a wide variety of products. Foamed (cellular or expanded) products are of interest because of their use in various building and automotive applications, in which fire performance is a concern. Expanded polymers of vinyl aromatic polymers and butadiene polymers and copolymers, as described before, are of particular interest. Non-cellular polymers can also be made in accordance with the invention.

The following examples are provided to illustrate the invention, but not to limit the scope thereof. All parts and percentages are by weight unless otherwise indicated.

Example 1

To a stirred solution of 5,5-dimethyl-2-thioxo-[1,3,2]dioxaphosphorinane-2-thiol (10.0 g, 50 mmol) in toluene (70 mL) is added triethylamine (5.0 g, 50 mmol), to form the trimethylammonium salt. The mixture is warmed to 45° C. To the resulting mixture is added 1,4-dibromobut-2-ene (5.34 g, 25 mmol) and the mixture is heated at reflux for 1 hour. The solution is then washed with saturated aqueous sodium bicarbonate solution (50 mL), dried over anhydrous magnesium sulfate and concentrated under reduced pressure to yield a white solid. The crude product is slurried in ethanol (40 mL) and filtered to yield 8.7 g (80%) of a white solid, 2,2'-[2-butene-1,4-diylbis(methylthio)]bis[5,5-dimethyl-1,3,2-dioxaphosphorinane]-2,2'-disulfide, having the structure:

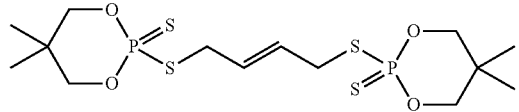

The thermal stability of the 2,2'-[2-butene-1,4-diylbis(methylthio)]bis[5,5-dimethyl-1,3,2-dioxaphosphorinane]-2,2'-disulfide is evaluated by thermogravimetric analysis as described before. The sample exhibits a 5% WLT of 241° C. on this test. Proton and $^{31}$P NMR on the sample show the following peaks:

$^1$H NMR (300 MHz, CDCl$_3$,) δ: 5.82 (m, 2H), 4.17 (m, 4H), 3.95 (m, 4H), 3.62 (m, 4H), 1.24 (s, 6H), 0.93 (s, 6H). $^{31}$P NMR (CDCl$_3$ vs. H$_3$PO$_4$) δ: 89.23.

A portion of the sample is melt blended with a polystyrene resin at a 4:96 weight ratio. The solidified melt blends are ground using a Wiley lab grinder and a 3 millimeter (mm) screen size. 25-27 g aliquots of the ground melt blends are compression molded into plaques measuring 100 mm×100 mm×1.5 mm using a Pasadena Hydraulic Platen Press (Model # BL444-C-6M2-DX2357) operating at a set point temperature of 180° C. with a pressure application time of 5 min and an applied pressure of 25,000 pounds per square inch (psi) (172 MPa). The molded plaques are cut into strips for Limiting Oxygen Index (LOI) and FP-7 testing. LOI is evaluated according to ASTM D 2863, and is found to be 26.5%. FP-7 is evaluated as described before and found to be 1.9 s.

A concentrate of 10 wt %, based on concentrate weight, of the phosphorus-sulfur additive in polystyrene is prepared by blending the 2,2'-[2-butene-1,4-diylbis(methylthio)]bis[5,5-dimethyl-1,3,2-dioxaphosphorinane]-2,2'-disulfide and polystyrene. The blend is melt compounded with the polystyrene using a Haake RHEOCORD™ 90 conical twin screw extruder equipped with a stranding die. The extruder has three temperature zones operating at set point temperatures of 135° C., 170° C. and 180° C. and a die set point temperature of 180°

C. The extruded strands are cooled in a water bath and cut into pellets approximately 5 mm in length. The pellets are converted into a foam using, in sequence, a 25 mm single screw extruder with three heating zones, a foaming agent mixing section, a cooler section and an adjustable 1.5 mm adjustable slit die. The three heating zones operate at set point temperatures of 115° C., 150° C. and 180° C. and the mixing zone operates at a set point temperature of 200° C. Carbon dioxide (4.5 parts by weight (pbw) per 100 pbw combined weight of the concentrate pellets and the additional polystyrene pellets) is fed into the foaming agent mixing section using two different RUSKA™ (Chandler Engineering Co.) syringe pumps. Concentrate pellets and pellets of additional polystyrene are dry blended together with 0.05 wt %, based on dry blend weight, of barium stearate as a screw lubricant. The ratio of the concentrate pellets and pellets of additional polystyrene are selected to provide a final concentration of FR additive of 4.2% by weight. The dry blend is added to the extruder's feed hopper and fed at a rate of 2.3 kg/hr. Pressure in the mixing section is maintained above 1500 psi (10.4 MPa) to provide a polymer gel having uniform mixing and promote formation of a foam with a uniform cross-section. The coolers lower the foamable gel temperature to 120° C. to 130° C. The die opening is adjusted to maintain a die back pressure of at least 1000 psi (6.9 MPa). The foamable gel expands as it exits the die to form a polystyrene foam having a bulk density of ~2.5 pcf (~40 kg/m$^3$). LOI for the foam is 24.7%, and FP-7 is 4.9 seconds.

Example 2

A mixture of N,N-diethylethanaminium, 5,5-dimethyl-1,3,2-dioxaphosphorinane-2-thiolate-2-oxide (7.5 g, 27 mmol) and 1,4-dibromobutene (2.84 g, 13.2 mmol) is slurried in 50 mL of ethanol and refluxed for 5 hours. The reaction mixture is cooled and concentrated under reduced pressure. The resulting residue is dissolved in methylene chloride (100 mL), washed with water (40 mL), dried and concentrated to yield 3.60 g (66%) of white solid, 2,2'-[2-butene-1,4-diylbis(methylthio)]bis[5,5-dimethyl-1,3,2-dioxaphosphorinane]-2,2'-dioxide, having the structure:

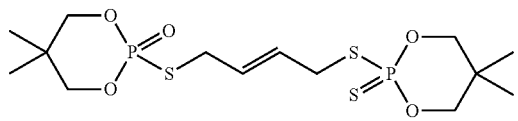

The 5% WLT for this material is 255° C. Plaques made from a blend of 4% of the product in 96% polystyrene have an LOI of 22% and an FP-7 value of 5.7 s.

Example 3

To a stirred solution of the ammonium salt of dithiophosphoric acid O,O-diethyl ester (15.8 g, 78 mmol) in ethanol (130 mL) at 80° C. is added 1,4-dibromo-2-butene (7.55 g, 35 mmol) in portions. The resulting mixture is cooled, diluted with water (150 mL) and extracted with methylene chloride (3×100 mL). The organic layer is dried over anhydrous magnesium sulfate, filtered and concentrated under reduced pressure to yield 15 g (99%) of S-[4-(diethoxy-thiophosphorylsulfanyl)-but-2-enyl]dithiophosphoric acid O,O'-diethyl ester, having the structure:

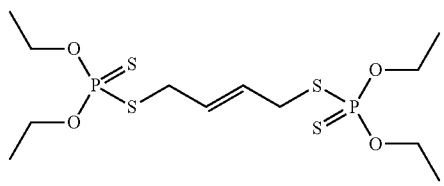

Example 4

To a stirred solution of 5,5-dimethyl-2-thioxo-[1,3,2]dioxaphosphorinane-2-thiol (8.0 g, 40 mmol) in toluene (70 mL) is added triethylamine (4.0 g, 40 mmol). The mixture is warmed to 45° C. To the resulting mixture is added o-xylyl-dichloride (3.51 g, 20 mmol) and the mixture is then heated to reflux for 1 hour. The solution is washed with saturated aqueous sodium bicarbonate solution (50 mL), dried over anhydrous magnesium sulfate and concentrated under reduced pressure to yield a white solid. The crude product is slurried in ethanol (40 mL) and filtered to yield 7.8 g (78%) of white solid, 2,2'-[1,2-phenylenebis(methylthio)]bis[5,5-dimethyl-1,3,2-dioxaphosphorinane]-2,2'-disulfide, having the structure:

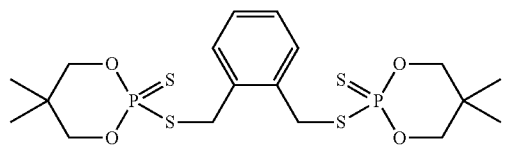

The 5% WLT for this material is 240° C. Proton, $^{13}$C and $^{31}$P NMR on the sample show the following peaks:

$^1$H NMR (CDCl$_3$) δ: 7.40 (m, 2H), 7.25 (m, 2H), 4.32 (d, J=12 Hz, 4H), 4.11 (m, 4H), 3.88 (m, 4H), 1.24 (s, 6H), 0.86 (s, 6H).

$^{13}$C NMR (CDCl$_3$) δ: 135.22, 135.12, 131.20, 128.76, 77.75, 77.64, 34.57, 34.54, 32.72, 32.64, 22.34, 22.14.

$^{31}$P NMR (CDCl$_3$) δ: 87.49.

Plaques made from a blend of 3% of the product in 97% polystyrene have an LOI of 23% and an FP-7 value of 3.5 s. Polystyrene foam made from the same blend exhibits an LOI of 23.3% and an FP-7 value of 5.3 s.

Example 5

A mixture of N,N-diethylethanaminium, 5,5-dimethyl-1,3,2-dioxaphosphorinane-2-thiolate-2-oxide (6.2 g, 22 mmol) and o-xylyl dichloride (1.94 g, 11 mmol) is slurried in 50 mL of ethanol and refluxed for 5 hours. The reaction mixture is cooled and concentrated under reduced pressure. The resulting residue is dissolved in methylene chloride (100 mL), washed with water (40 mL), dried and concentrated to yield 3.6 g (70%) of a white solid, 2,2'-[1,2-phenylenebis(methylthio)]bis[5,5-dimethyl-1,3,2-dioxaphosphorinane]-2,2'-dioxide, having the structure:

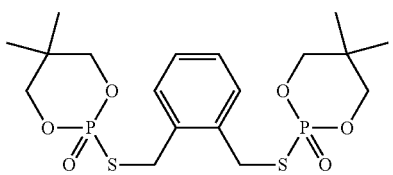

The 5% WLT for this material is 247° C. Plaques made from a blend of 2.5% of the product in 97.5% polystyrene have an LOI of 21.5 and an FP-7 value of 11.4 s.

Example 6

O,O)-diethyldithiophosphate ammonium salt (14.13 g, 69.50 mmol) is weighed into a beaker and then dissolved in ethanol (130 mL). The beaker is then placed into a hot water bath (80° C.) and set stirring. When the contents in the beaker reach 80° C., '-dichloro-o-xylene (5.53 g, 31.59 mmol) is added portionwise. The reaction is stirred for 3 hours at 80° C., after which time the reaction beaker contains precipitated ammonium chloride. The contents of the beaker are poured into a separatory funnel and deionized water is added to dissolve the ammonium chloride. Methylene chloride is used (3 times) to extract the product S,S'-(1,2-phenylenedimethylene)-O,O,O',O',-tetraethyl phosphorodithioate out of the aqueous/ethanol phase. The isolated organic phase is dried over anhydrous $MgSO_4$. The methylene chloride is filtered from the $MgSO_4$ and dried on a rotavap, leaving an oil. The oil is then placed under vacuum for several hours to remove any remaining ethanol. After leaving the oil for several days, crystals of S,S'-(1,2-phenylenedimethylene)-O,O,O',O',-tetraethyl phosphorodithioate form in the flask. These crystals are isolated and found to have a melting point of 33-34.5° C. The product has a 5% WLT of 225° C. An idealized reaction schematic is as follows:

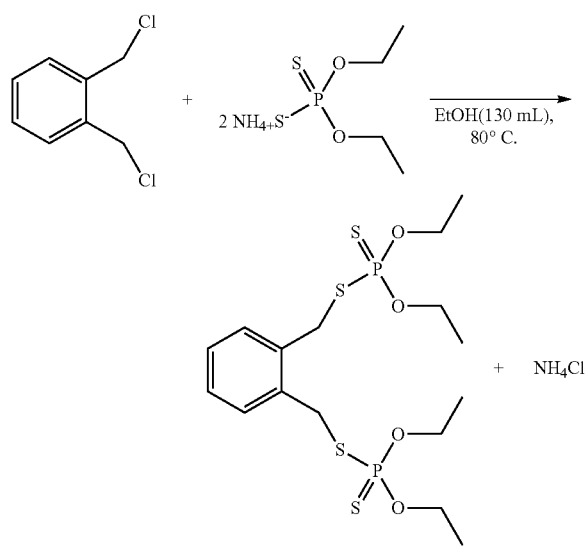

Example 7

To a stirred solution of 5,5-dimethyl-2-thioxo-[1,3,2]dioxaphosphorinane-2-thiol (9.70 g, 48 mmol) in toluene (110 mL) is added triethylamine (4.80 g, 48 mmol). The mixture is warmed to 45° C. To the resulting mixture is added 1,2,4,6-tetra(bromomethyl)benzene (5.0 g, 11 mmol) and the mixture is heated to reflux for 14 hours. The toluene solution is then filtered, and the precipitate is slurried in saturated aqueous sodium bicarbonate solution (100 mL). The precipitate is filtered, dried to yield a white solid, 2,2',2'',2'''-[1,2,4,6-phenylenetetra(methylthio)]tetra[5,5-dimethyl-1,3,2-dioxaphosphorinane]-2,2',2'',2'''-sulfide. The yield is 9.4 g (93%). The structure of the product is:

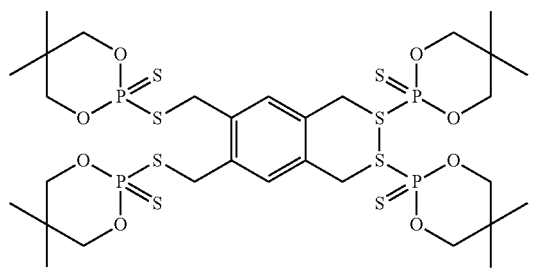

The 5% WLT for this material is 281° C. Plaques made from a blend of 2.8% of the product in 97.2% polystyrene have an LOI of 24.3% and an FP-7 value of 5.6 s.

Example 8

To a stirred solution of 5,5-dimethyl-2-thioxo-[1,3,2]dioxaphosphorinane-2-thiol (8.19 g, 41 mmol) in toluene (110 mL) is added triethylamine (4.2 g, 41 mmol). The mixture is warmed to 45° C. To the resulting mixture is added 1,3,5-tris(bromomethyl)-2,4,6-trimethylbenzene (5.0 g, 13 mmol) and the mixture is heated to reflux for 14 hours. The solution is then diluted with methylene chloride (150 mL), washed with saturated aqueous sodium bicarbonate solution (100 mL), dried over anhydrous magnesium sulfate and concentrated under reduced pressure to yield a white solid. The crude product is recrystallized from acetonitrile to yield 8.0 g (85%) of white solid, 2,2',2''-[2,4,6-trimethyl-1,3,5-phenylenetris(methylthio)]tris[5,5-dimethyl-1,3,2-dioxaphosphorinane]-2,2',2''-disulfide. The structure of the product is:

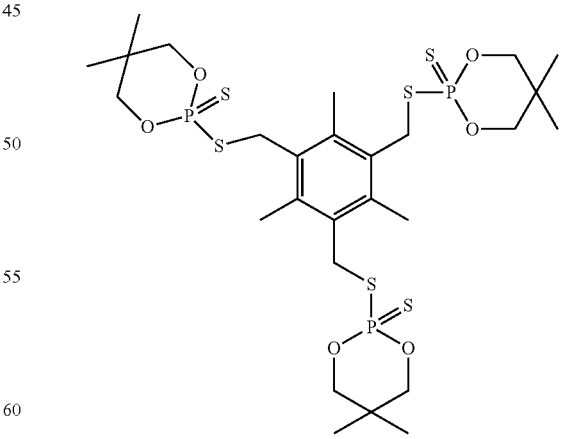

The 5% WLT for this material is 283° C. Plaques made from a blend of 3.1% of the product in 96.9% polystyrene have an LOI of 24.2% and an FP-7 value of 2.8 seconds. Polystyrene foam (2.54 pcf, ~40 $kg/m^3$ density) made from the same blend exhibits an LOI of 27% and an FP-7 value of 1.1 s.

Example 9

An epoxy novolac resin having a reported $M_n$ of 570 and approximately 3.6 epoxide units/molecule (10.4 g) is dissolved in 50 mL toluene with stirring. To this is added 11.2 g of 5,5-dimethyl-2-mercapto-1,3,2-dioxaphosphorinane 2-sulfide, along with an additional 40 mL of toluene. The mixture is stirred under nitrogen. After 30 minutes, 50 mL of methylene chloride is added to form a homogeneous mixture. After stirring 18 hours at room temperature, the product is recovered by precipitation in 600 mL of hexane. The product is dried overnight in vacuum oven at 70° C. The idealized reaction is represented schematically as follows:

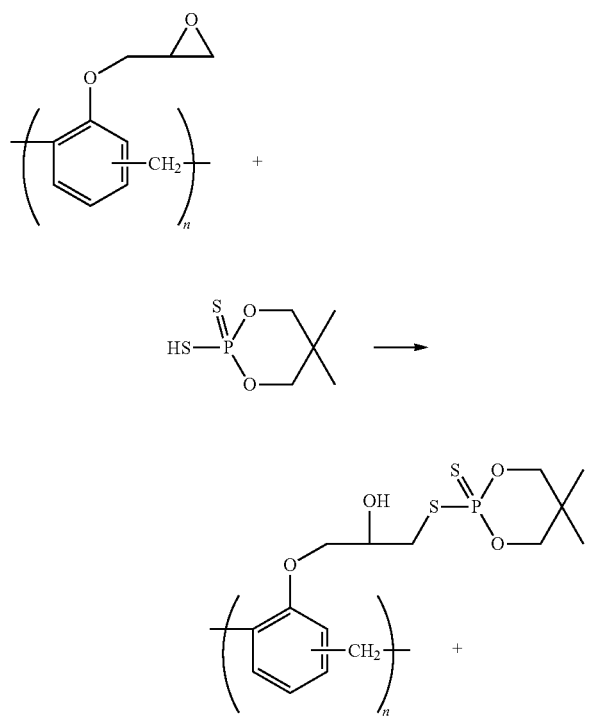

5% WLT for this material is 239° C.

Example 10

An unsaturated polyester is prepared from cyclohexanedimethanol (50/50 mixture of 1,4 and 1,3-isomer), dimethyl maleate and isophthalic acid. The mole ratio of maleate/isophthalate is 48:52, the weight average molecular weight of the unsaturated polyester (by GPC, relative to polystyrene) is 2620 and its glass transition temperature ($T_g$) is 20° C. The unsaturated polyester (30.0 g) and anhydrous pyridine (4 ml) are dissolved in 100 ml methylene chloride, and to the solution is added terephthaloyl chloride (4.5 g). After stirring under nitrogen for 1 hour, methanol (5 ml) is added. The polymer solution is washed with 100 ml of 1.0 N HCl, and the product is isolated by precipitation in methanol (1 liter). The product is dried overnight in a vacuum oven at 50° C. The resulting unsaturated polyester (15.0 g) and 5,5-dimethyl-2-mercapto-1,3,2-dioxaphosphorinane 2-sulfide (8.0 g, 40 mmol) are dissolved in 20 mL of 1,2-dichloroethane and the solution is refluxed for 19 hours. The solution is diluted by addition of 75 mL of 1,2-dichloroethane, and the product is isolated by precipitation in 500 mL of methanol. The product is dried overnight in a vacuum oven at 50° C. The weight average molecular weight of the product is 5620. Its $T_g$ is 50° C. 5% WLT for this product is 276° C. The idealized structure of the repeat units of the polymer is represented as:

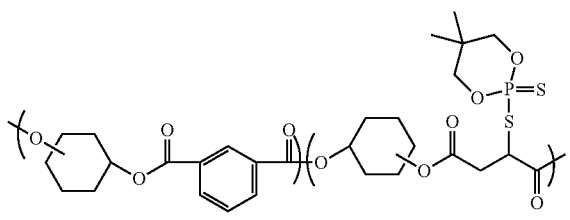

Plaques made from a blend of 19% of the product in 81% polystyrene have an LOI of 24.3 and an FP-7 value of 1.3.

Example 11

To a 500 mL three necked round bottom flask equipped with a stir shaft, a reflux condenser with nitrogen inlet and an addition funnel is added 38.18 g (0.195 mol) of 5,5-dimethyl-2-mercapto-1,3,2-dioxaphosphorinane-2-sulfide and 60 mL of toluene to form a white slurry. The flask is then heated to 85° C. to form a solution. A styrene-butadiene-styrene (SBS) triblock copolymer (10 g, 0.097 mol) dissolved in 80 mL of toluene at room temperature is then added dropwise over 40 minutes to the heated solution. The SBS copolymer used in this example contains a central polybutadiene block having an average of 53 monomer units, of which about 22% are 1,4-butadiene units and 78% are 1,2-butadiene units. The terminal polystyrene blocks are 23-24 monomer units in length, on average. The reaction is then allowed to stir under nitrogen for 68 hours at 85° C. The reaction solution is then cooled, diluted with 200 mL of toluene and washed twice with KOH (aq) and once with water. The polymer solution is then precipitated into methanol and dried for 5 hours in a vacuum oven at 40° C. The polymer is re-dissolved in 200 mL of toluene, washed twice with water, dried over $MgSO_4$, precipitated a second time into 2 L of methanol and dried overnight in a vacuum oven at 40° C. 19.36 g of white polymer powder is collected (67.12% yield). The idealized reaction can be represented schematically as follows:

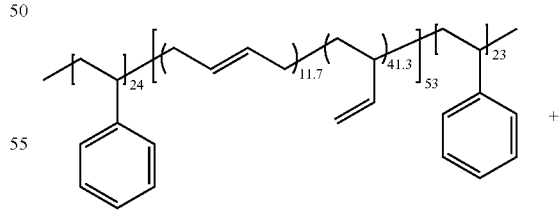

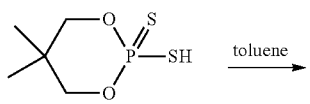

-continued

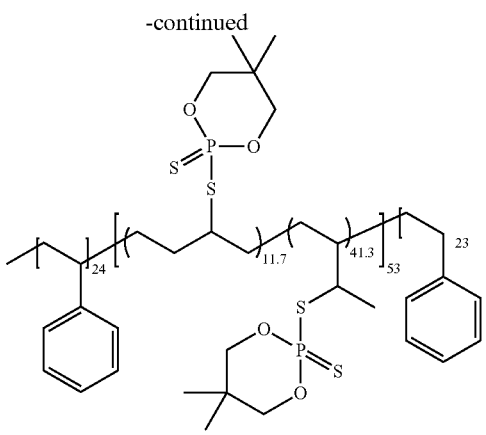

Proton NMR in CDCl₃ shows that 5% of the aliphatic double bonds in the starting polymer remain unreacted. GPC analysis in THF versus polystyrene standards shows that a small amount of polymer coupling occurs, as the product has an $M_n$ of 128,560 and an $M_w$ of 147,330.

The 5% WLT for the product is 242° C. Plaques made from a blend of 3.6% of the product in 96.4% polystyrene have an LOI of 24.2 and an FP-7 value of 4.2.

Example 12

Phosphorus-sulfur groups are introduced onto an SB diblock copolymer in a manner analogous to that described in Example 11. To a 500 mL three necked round bottom flask equipped with a stir shaft, a reflux condenser with nitrogen inlet and an addition funnel is added 27.85 g (0.14 mol) of 5,5-dimethyl-2-mercapto-1,3,2-dioxaphosphorinane-2-sulfide and 45 mL of toluene (white slurry). The reaction mixture is immersed into an oil bath set to 85° C. and the 5,5-dimethyl-2-mercapto-1,3,2-dioxaphosphorinane 2-sulfide dissolves in the toluene. Styrene-butadiene diblock copolymer (10 g of polymer, 0.07 mol of polybutadiene block) dissolved in 80 mL of toluene at room temperature is then added dropwise over 35 minutes to the heated solution. The reaction is allowed to heat and stir under nitrogen for 70 hours. The reaction solution is cooled, diluted with 200 mL of toluene and washed twice with aqueous KOH and once with water. The polymer is precipitated into 2 L of methanol and dried overnight under vacuum at 70° C. The polymer is re-dissolved in 250 mL of toluene, dried over MgSO₄, filtered, precipitated into 2 L of methanol and dried overnight in a vacuum oven at 70° C. 18.13 g of white polymer powder is collected (76% yield).

The SB diblock copolymer in this example has a polybutadiene block with an average length of 38 monomer units. About 29% of the butadiene units are 1,4-units. The polystyrene block is about 62 units in length. The product is represented by the idealized structure, which does not reflect 1,2- and 1,4-butadiene structures in the product, as follows:

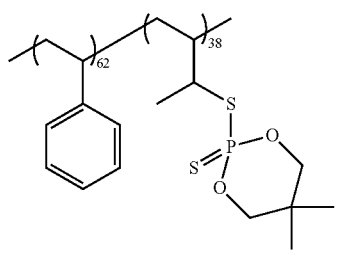

The 5% WLT temperature for this product is 260° C. Plaques made from a blend of 8.4% of the product in 91.6% polystyrene have an LOI of 25 and an FP-7 value of 1.3 seconds.

Example 13

To a 500 mL three necked round bottom flask equipped with a stir shaft, a reflux condenser with nitrogen inlet and an addition funnel are added 19.82 g (0.10 mol) of 5,5-dimethyl-2-mercapto-1,3,2-dioxaphosphorinane 2-sulfide and 45 mL of toluene to form a white slurry. Triethylamine (10.12 g, 0.10 mol) is added to the slurry, and the slurry is heated to 45° C. to form a solution. Poly(vinylbenzylchloride) (15 g, 0.098 mol) dissolved in 80 mL of toluene at room temperature is then added dropwise to the heated solution. After the polymer addition is complete, the reaction mixture is heated to reflux for 100 minutes. The reaction solution is cooled, diluted with 100 mL of chloroform and washed four times with 300 mL of water. The polymer solution is then dried over MgSO₄, filtered, concentrated and precipitated into 2 L of methanol. The resulting white polymer powder is collected via filtration and dried overnight in a vacuum oven at 70° C. to yield 27.2 g of product. The idealized reaction scheme is represented as follows:

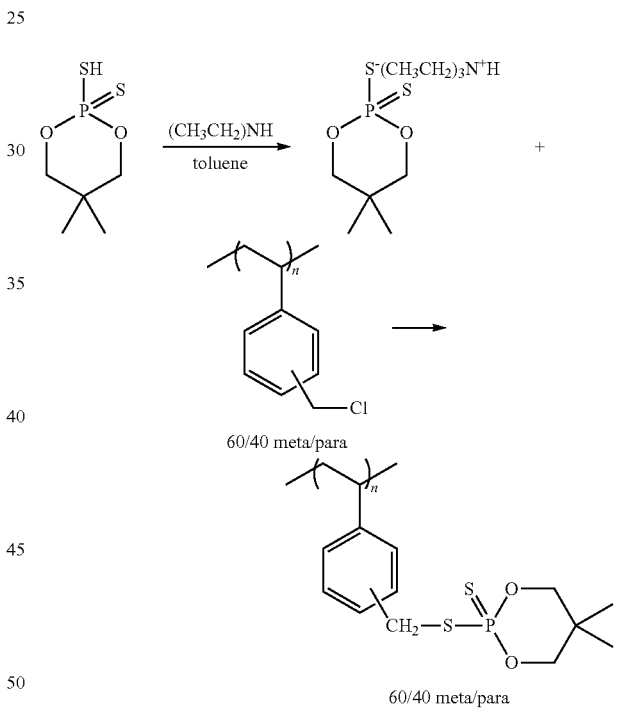

The product has an $M_n$ of 51,859, an $M_w$ of 120,880 and a PDI of 2.33, as measured by GPC in THF against polystyrene standards. Its 5% WLT is 292° C. Plaques made from a blend of 3.8% of the product in 96.2% polystyrene have an LOI of 22 and an FP-7 value of 3.8.

Example 14

To a 500 mL three necked round bottom flask equipped with a stir shaft, a reflux condenser with nitrogen inlet and an addition funnel are added 41.82 g (0.21 mol) of 5,5-dimethyl-2-mercapto-1,3,2-dioxaphosphorinane-2-sulfide and 60 mL of toluene to form a white slurry. The slurry is heated to 85° C. to form a solution. A styrene-butadiene-styrene (SBS) triblock co-polymer (10 g, 0.105 mol) dissolved in 80 mL of toluene at room temperature is then added dropwise over 40 minutes to the heated solution. 10% of the butadiene units in this polymer are 1,2-butadiene units, and 90% are 1,4-butadiene units. The reaction mixture is stirred under nitrogen for 71 hours at 85° C. The reaction solution is then cooled, diluted with 400 mL of toluene and washed twice with aqueous KOH and once with water. The polymer solution is then dried over MgSO$_4$, precipitated into 2 L of methanol and dried overnight in a vacuum oven at 40° C. The product polymer (23 g) is dissolved in 1 L of tetrahydrofuran (THF) to form a cloudy white solution, which is filtered through a 0.45 μm HVHP filter using 10-20 psi air pressure. The clear polymer filtrate is precipitated a second time into 2 L of methanol. The white polymer product is collected via filtration and dried overnight in a vacuum oven at 40° C. 13.4 g of white polymer powder is collected (43.5% yield). The idealized reaction scheme is represented as follows:

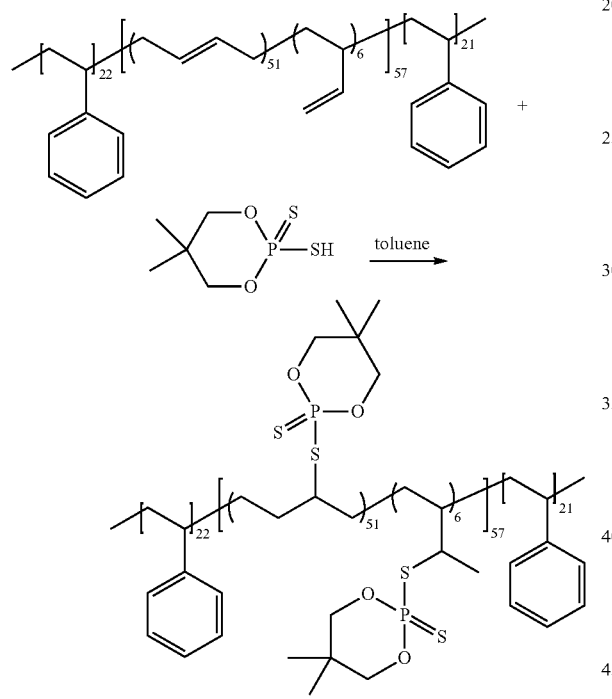

Proton NMR in CDCl$_3$ shows that 11.7% of the aliphatic carbon-carbon double bonds in the original polymer remain unreacted. GPC analysis in THF versus polystyrene standards shows that a small amount of polymer coupling has occurred. The product has an M$_n$ of 124,860, an M$_w$ of 137,030, and a polydispersity of 1.097. The 5% WLT for the product is 244° C. Plaques made from a blend of 3.6% of the product in 96.4% polystyrene have an LOI of 22.3% and an FP-7 value of 4.2 seconds.

Example 15

To a 250 mL three necked round bottom flask equipped with a stir shaft, a reflux condenser with nitrogen inlet and an addition funnel are added 8.36 g (0.042 mol) of 5,5-dimethyl-2-mercapto-1,3,2-dioxaphosphorinane 2-sulfide, 3 g of styrene-butadiene-styrene (SBS) triblock copolymer (0.021 mol of polybutadiene block) and 40 mL of toluene to form a white slurry. The reaction mixture is immersed into an oil bath set to 110° C. and all solids dissolve in the toluene. The reaction mixture is allowed to heat and stir under nitrogen for 69 hours. The reaction solution is cooled to 40° C. and diluted with 50 mL of toluene. Triethylamine (2.98 mL, 0.021 mol) is added directly to the crude solution and the reaction is allowed to stir under nitrogen at 40° C. for 1 hour, during which time a precipitate forms. The crude mixture is run through a plug of silica and the polymer filtrate is concentrated via rotor evaporation. The polymer solution is then precipitated into 1 L of methanol and dried overnight under vacuum at 70° C. 5.78 g of white polymer powder is collected (80.5% yield).

The idealized reaction scheme is as follows:

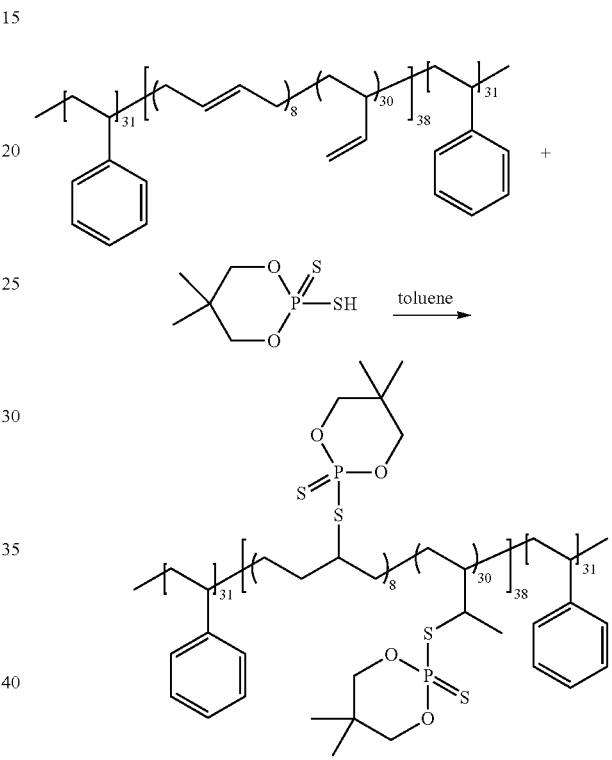

The 5% WLT for this material is 248° C. Plaques made from a blend of 7.8% of the product in 92.2% polystyrene have an LOI of 24.5 and an FP-7 value of 0.9 seconds.

Example 16

To a stirred solution of the triethylammonium salt of the 5,5-dimethyl-2-thioxo-[1,3,2]dioxaphosphorinane-2-thiol (18.77 g, 63 mmol) in 150 mL of pyridine is added trischloromethyl phosphine oxide (3.50 g, 18 mmol). The mixture is heated to 105° C. for 2 hours. The resulting dark yellow solution is diluted with methylene chloride (300 mL), washed with water (1 L), dilute HCl solution (1 M, 250 mL) and saturated aqueous sodium bicarbonate solution. The organic layer is dried over anhydrous magnesium sulfate and concentrated under reduced pressure to yield a light yellow solid. The resulting crude material is first purified by slurrying in warm acetonitrile and chilling in ice bath followed by filtration to yield a pale yellow solid. Recrystallization from methanol yields 3.96 g (33% yield) of the white product, tris[2-methylenethio-(5,5-dimethyl-1,3,2-dioxaphosphorinane-2-thioxo) phosphine oxide, which is represented by the structure.

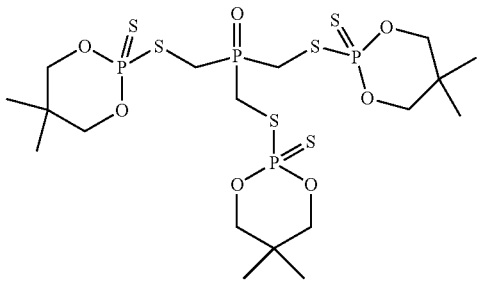

The 5% WLT for the product is 243° C. Plaques made from a blend of 2.7% of the product in 97.3% polystyrene have an LOI of 22.8 and an FP-7 value of 4.4 seconds.

Example 17

A mixture of cyanuric chloride (1.84 g, 10 mmol) and the ammonium salt of 5,5-dimethyl-2-thioxo-[1,3,2]dioxaphosphorinane-2-thiol (7.10 g, 33 mmol) in 75 mL of acetonitrile is refluxed for 4 hours. The reaction mixture is cooled and concentrated under reduced pressure. The resulting solid is diluted with 150 mL of methylene chloride and washed with aqueous saturated sodium bicarbonate solution (100 mL). The organic layer is dried over anhydrous magnesium sulfate and concentrated under reduced pressure to yield a yellow solid. This material is purified by dissolving in methylene chloride (100 mL), filtering through silica gel and removing the solvent under reduced pressure to yield 4.60 g (67%) of a white solid, 2,2',2"-[s-triazine-2,4,6-tris(thio)]tris[(5,5-dimethyl-1,3,2-dioxaphosphorinane)-2,2',2"-sulfide], having the structure:

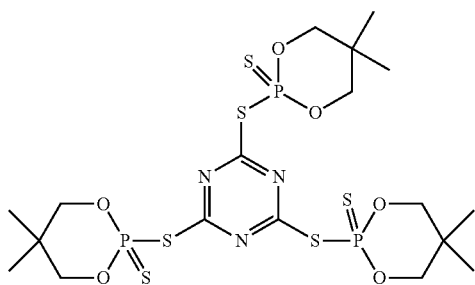

The 5% WLT for the product is 249° C. Plaques made from a blend of 2.7% of the product in 97.3% polystyrene have an LOI of 23.8 and an FP-7 value of 4 seconds.

Example 18

Sulfur (3.52 g, 110 mmol) is added in portions to a solution of N-benzyl-N-5,5-dimethyl-1,3,2-dioxaphosphorinan-2-yl)-5,5-dimethyl-1,3,2-dioxaphosphorinan-2-amine (10.2 g, 27 mmol) and the mixture is allowed to stir overnight. The reaction mixture is concentrated under reduced pressure. The residue is slurried in chloroform (100 mL), filtered and the filtrate is stored in a freezer overnight. The cold reaction mixture is filtered again and the filtrate is concentrated to yield a white solid. Recrystallization of this solid in ethanol provides 4.81 g (40%) of white solid, N-benzyl-N-(5,5-dimethyl-2-sulfido-1,3,2-dioxaphosphorinan-2-yl)-5,5-dimethyl-1,3,2-dioxaphosphorinan-2-amine-2-sulfide, having the structure:

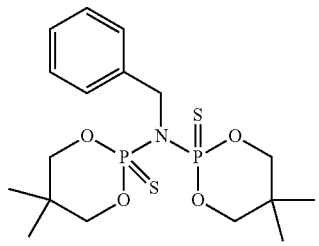

The 5% WLT for this material is 202° C. Plaques made from a blend of 4.8% of the product in 95.2% polystyrene have an LOI of 23 and an FP-7 value of 1.1 s.

Example 19

A mixture of neopentyl glycol (13.8 g, 132 mmol) and o-xylyltetrachlorothiophosphate (24.7 g, 66 mmol) is slurried in chlorobenzene (250 mL) containing pyridine (1 mL) and heated to 115° C. for 10 hours. An aliquot is checked by $^{31}$P NMR and found to still contain the starting materials. The reaction mixture is heated and stirred for another 15 hours. The reaction mixture is concentrated under reduced pressure to yield a sticky brown solid. The solid is dissolved in 120 mL of an ethyl acetate/hexane (1:1) mixture and chromatographed over silica gel to yield a yellowish brown solid (20.5 g). The solid is washed with an ethyl acetate:hexane mixture (1:3, 50 mL) to yield 7 g of an off-white solid. Another 2 g of material is recovered by concentrating the filtrate and washing that with the ethyl acetate:hexane mixture. The combined yield is 32% of [1,2-phenylenebis(methylene)]bis[5,5-dimethyl[1,3,2]dioxaphosphorinane]2,2'-disulfide, having the structure:

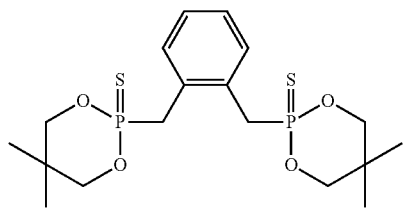

The 5% WLT for this material is 284° C. Plaques made from a blend of 5.1% of the product in 94.9% polystyrene have an LOI of 22.8 and an FP-7 value of 1.2 s.

Example 20

A mixture of 1,4-dibromobutane (2.42 g, 11 mmol) and the ammonium salt of 5,5-dimethyl-2-thioxo-[1,3,2]dioxaphosphorinane-2-thiol (6.50 g, 30 mmol) in 50 mL of ethanol is refluxed for 4 hours. The reaction mixture is then cooled, diluted with 100 mL of chloroform and washed with aqueous saturated sodium bicarbonate solution (100 mL). The organic layer is dried over anhydrous magnesium sulfate and concentrated under reduced pressure to yield 4.71 g (93%) of a white solid, 2,2'-[1,4-butylbis(methylthio)]bis[5,5-dimethyl-1,3,2- dioxaphosphorinane]-2,2'-disulfide. The product has the following structure:

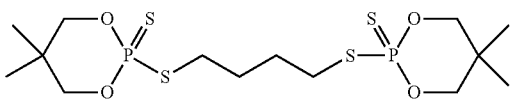

The 5% WLT for this material is 244° C. Plaques made from a blend of 2.9% of the product in 97.1% polystyrene have an LOI of 22.6 and an FP-7 value of 7.1 seconds.

Example 21

Bicyclo[2,2,1]2,5-heptadiene (0.92 g, 10 mmol) is added to a stirred solution of 5,5-dimethyl-2-thioxo-[1,3,2]dioxaphosphorinane-2-thiol (4.0 g, 20 mmol) in 40 mL of toluene. An exothermic reaction ensues, driving the temperature of the reaction mixture to 56° C. with the formation of white precipitate. The reaction mixture is further warmed to 70° C. for an hour and allowed then to cool to room temperature. Filtration of the mixture provides 4.5 g of the product, 2,2'-[bicyclo [2.2.1]heptane-2,5-diylbis(thio)]bis[5,5-dimethyl-1,3,2-dioxaphosphorinane]2,2'-disulfide. The compound is characterized by LC/MS methods as being the bis-adduct, having the structure:

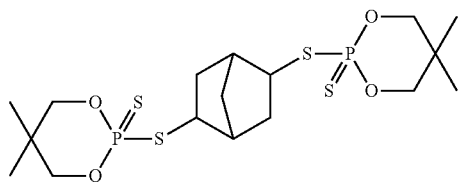

The 5% WLT for this material is 264° C. Plaques made from a blend of 3% of the product in 97% polystyrene have an LOI of 23 and an FP-7 value of 3.9 seconds.

Example 22

A mixture of pentaerythritol triacrylate and pentaerythritol tetraacrylate having an average acrylate functionality of 3.4 and an equivalent weight of 89.34 g/equivalent is added into a 500 mL single necked round bottom flask equipped with magnetic stirring and a nitrogen inlet, together with 100 mL of methylene chloride. 5,5-dimethyl-2-thioxo-[1,3,2]dioxaphosphorinane-2-thiol (10.96 g, 0.055 mole) is added and the resulting homogeneous solution is allowed to stir for 48 hours. Additional 5,5-dimethyl-2-thioxo-[1,3,2]dioxaphosphorinane-2-thiol (1.0 g, 0.005 mole) is added and the mixture is allowed to stir for an additional 48 hours. At this point, NMR analysis shows that 93% of the acrylate groups have reacted. The solvent is removed from the reaction mixture via a rotary evaporator heated to 80° C. The remaining material is placed into an 80° C. vacuum oven for ~16 hours. 13.6 g (85% isolated yield) of a clear, water-white glassy material is recovered. The idealized reaction scheme (to form the tetra adduct) is as follows:

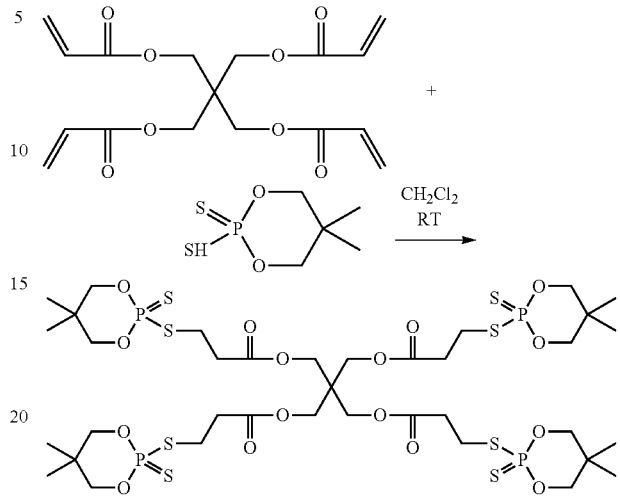

The 5% WLT for this material is 274° C. Plaques made from a blend of 3.5% of the product in 96.5% polystyrene have an LOI of 23.3 and an FP-7 value of 3.5 seconds.

Example 23

To a 250 mL 3-neck round bottom flask is added diethyl maleate (0.1 mole, 17.2 g). 5,5-dimethyl-2-thioxo-[1,3,2]dioxaphosphorinane-2-thiol (0.1 mole, 19.8 g) is added with stirring, and the resulting mixture is heated for 2 hours at 100° C. The idealized reaction scheme is as follows:

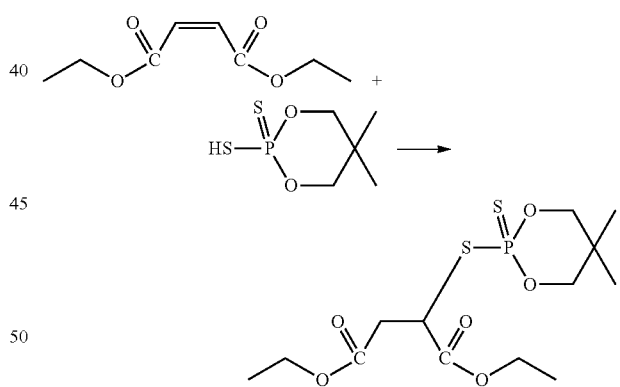

The 5% WLT for this product is 218° C. Plaques made from a blend of 4.6% of the product in 95.4% polystyrene have an LOI of 23.2 and an FP-7 value of 0.2 seconds.

Example 24

A stirred solution of 1,9-decadiene (5.0 g, 36.1 mmol) and 5,5-dimethyl-2-thioxo-[1,3,2]dioxaphosphorinane-2-thiol (14.33 g, 72.3 mmol) in toluene (75 mL) is heated to 80° C. for 6 hours. $^{31}$P NMR of an aliquot shows the presence of starting thiol as well as the mono- and bis-adducts. The mixture is concentrated to half its volume and heated for another 6 hours at 80° C. The mixture is diluted with methylene chloride, extracted with aqueous saturated sodium bicarbonate, dried over anhydrous magnesium sulfate and concentrated under reduced pressure to yield an oil which slowly solidifies to yield 18.5 g (96%) of 2,2'-[decane-2,9-diylbis(thio)]bis(5,5-dimethyl-1,3,2-dioxaphosphorinane)2,2'-disulfide. The product has a structure as follows:

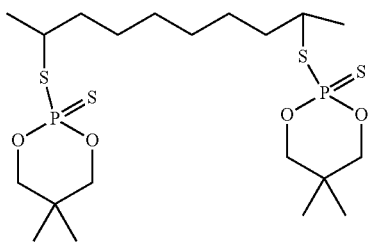

The 5% WLT for this product is 239° C. Plaques made from a blend of 6.3% of the product in 93.7% polystyrene have an LOI of 24.3 and an FP-7 value of 2.6 seconds.

Example 25

5,5-dimethyl-2-thioxo-[1,3,2]dioxaphosphorinane-2-thiol (8.0 g, 40.4 mmol) is dissolved in toluene (100 mL). Triethylamine (3.8 g, 40.4 mmol) is added and the mixture is allowed to stir for 10 minutes. Bromodiphenylmethane (10.5 g, 42.4 mmol) is then added, and the reaction mixture is warmed to 80° C. for 2 hours. HPLC of an aliquot shows most of the starting bromo compound is consumed. The reaction mixture is worked up by diluting it with methylene chloride (100 mL) and washing it with aqueous saturated sodium bicarbonate solution (100 mL). The organic layer is dried over anhydrous magnesium sulfate and concentrated under reduced pressure to yield a white solid. The crude material is recrystallized from toluene. The yield of 2-[(diphenylmethyl)thio]-5,5-dimethyl-1,3,2-dioxaphosphorinane 2-sulfide was 13.2 g (95%). The structure of the compound is as follows:

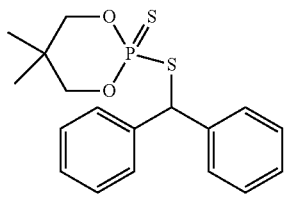

The 5% WLT for this product is 238° C. Plaques made from a blend of 8.3% of the product in 91.7% polystyrene have an LOI of 26 and an FP-7 value of 0.4 second.

Example 26

N,N-diethylethanaminium 6H-dibenz[c, e][1,2]oxaphosphorin-6-mercapto-6-oxide (8.0 g, 22.9 mmol) is dissolved in methylene chloride (75 mL) containing 1,4-dibromobut-2-ene (2.45 g, 11.5 mmol) and the resulting mixture is refluxed. After 3 hours of refluxing, most of the starting material is consumed. The reaction mixture is worked up by washing with saturated aqueous sodium bicarbonate solution (100 mL), dried over anhydrous magnesium sulfate and concentrated under reduced pressure to yield 4.6 g (73%) of 6,6'-[(2E)-but-2-ene-1,4-diylbis(thio)]bis(6H-dibenz[c,e][1,2] oxaphosphorin-6,6'-dioxide as a white solid with the following structure:

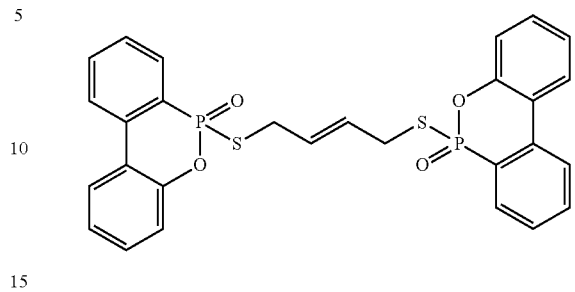

The 5% WLT for this product is 270° C. Plaques made from a blend of 6.4% of the product in 93.6% polystyrene have an LOI of 24.8 and an FP-7 value of 1 second.

Example 27

To a stirred solution of 1,4-bis[dimethyl[2-(5-norbornen-2-yl)ethyl]silyl]benzene (5.0 g, 11.5 mmol) in 40 mL of toluene is added 5,5-dimethyl-2-thioxo-[1,3,2]dioxaphosphorinane-2-thiol (4.56 g, 23 mmol). The mixture is warmed to 80° C. for 6 hours. The clear reaction mixture is then washed with aqueous sodium bicarbonate solution (100 mL), dried over anhydrous magnesium sulfate and concentrated under reduced pressure to yield an oil which slowly solidifies to a white solid (9.2 g, 96%). The structure of the product, 2,2'-{1,4-phenylenebis[(dimethylsilanediyl)ethane-2,1-diylbicyclo[2.2.1]heptane-6,2-diylthio]}bis(5,5-dimethyl-1,3,2-dioxaphosphorinane) 2,2'-disulfide, is as follows:

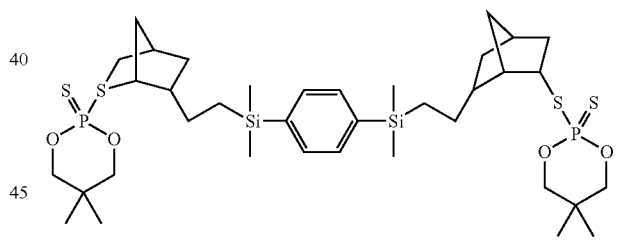

The 5% WLT for this product is 285° C. Plaques made from a blend of 4.9% of the product in 95.1% polystyrene have an LOI of 21.7 and an FP-7 value of 4.4 seconds.

Example 28

To a stirred solution of 5,5-dimethyl-2-thioxo-[1,3,2]dioxaphosphorinan-2-thiol (2.06 g, 10 mmol) in toluene (40 mL) is added triethylamine (0.10 g, 10 mmol). The mixture is warmed to 45° C. and 5,5-dimethyl-2[(4-chloromethylphenyl)methyl]-1,3,2-dioxaphosphorinane 2-oxide (3.00 g, 10 mmol) is added. The mixture is then heated to 90° C. for 4 hours. The solution is washed with saturated aqueous sodium bicarbonate solution (50 mL), dried over anhydrous magnesium sulfate and concentrated under reduced pressure to yield a white solid, 4.3 g (92%). The product, 2-({4-[(5,5-dimethyl-2-oxido-1,3,2-dioxaphosphorinan-2-yl)methyl]

benzyl}thio)-5,5-dimethyl-1,3,2-dioxaphosphorinane-2-sulfide, has the following structure:

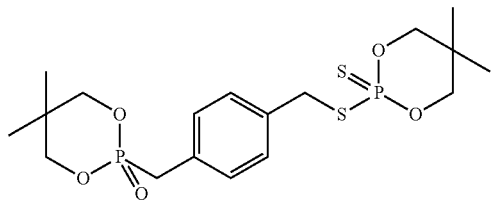

The 5% WLT for this material is 257° C. Plaques made from a blend of 4.8% of the product in 95.2% polystyrene have an LOI of 21.7 and an FP-7 value of 2.9 seconds.

Example 29

To a stirred suspension of 6H-dibenz[c, e][1,2]oxaphosphorin-6-oxide (10 g, 46.3 mmol) in 100 mL of toluene is added dropwise triethylamine (4.68 g, 46.3 mmol). Sulfur (1.48 g, 46.3 mmol) is then added in small portions. The reaction mixture is allowed to stir at 45° C. for 1 hour. o-Xylyl dichloride (4.05 g, 23.1 mmol) is added to the reaction mixture, which is then heated to 90° C. for 5 hours. The reaction mixture is cooled and worked up by concentrating it under reduced pressure and diluting the residue with methylene chloride (120 mL). The methylene chloride solution is washed with aqueous sodium bicarbonate solution (1×100 mL), dried over anhydrous magnesium sulfate, filtered and concentrated under reduced pressure to yield a white solid. The product is further purified by filtering through silica gel with methylene chloride and ethyl acetate (8:2) as the eluant, to yield 8.2 g (59%) of 6,6'-[1,2-phenylenebis(methylenethio)]bis(6H-dibenz[c, e][1,2]oxaphosphorin) 6,6'-dioxide, as a white solid with the following structure:

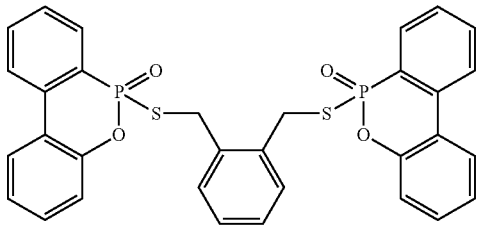

The 5% WLT for this material is 262° C. Plaques made from a blend of 7% of the product in 93% polystyrene have an LOI of 24.8 and an FP-7 value of 3.2 seconds.

Example 30

To a stirred suspension of 6H-dibenz[c, e][1,2]oxaphosphorin-6-oxide (10 g, 46.3 mmol) in 100 mL of toluene is added dropwise triethylamine (4.68 g, 46.3 mmol), followed by sulfur (1.48 g, 46.3 mmol) in small portions. The reaction mixture is allowed to stir at 45° C. for 1 hour. 1,3,5-tris (bromomethyl)-2,4,6-trimethylbenzene (6.09 g, 15.3 mmol) is added to the reaction mixture, after which it is heated to 90° C. for 5 hours. The reaction mixture is cooled and then worked up by concentrating it under reduced pressure and diluting the residue with methylene chloride (120 mL). The methylene chloride solution is washed with aqueous sodium bicarbonate solution (100 mL), dried over anhydrous magnesium sulfate, filtered and concentrated under reduced pressure to yield 13.1 g (95%) of the product, 6,6',6''-[(2,4,6-trimethylbenzene-1,3,5-triyl)tris(methylenethio)]tris(6H-dibenzo-[c, e][1,2]oxaphosphorin) 6,6',6''-trioxide, as an off-white solid. The proposed structure is as follows:

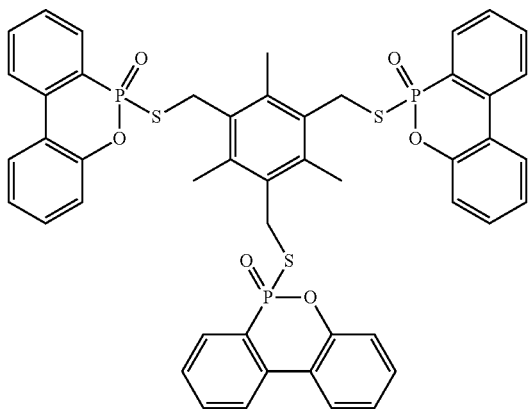

The 5% WLT for this material is 219° C. Plaques made from a blend of 6.2% of the product in 93.8% polystyrene have an LOI of 24.8% and an FP-7 value of 0.1 second.

Example 31

Tetraallyl pentaerythritol (6.03 g, 20.3 mmol) (prepared by the method of Nougier, R. M. and Mchich J., *Org. Chem.* 1985, 50, 3296-3298. "Alkylation of Pentaerythritol and Trimethylolpropane, Two Very Hydrophilic Polyols, by Phase-Transfer Catalysis") and 5,5-dimethyl-2-thioxo-[1,3,2]dioxaphosphorinane-2-thiol (19.91 g, 100.6 mmol are added to a 250 ml round bottom flask under nitrogen. The reaction mixture is heated for 48 hours whereupon NMR analysis shows complete conversion of the allyl groups on the starting material. The product is dissolved in a mixture of 50 mL of methylene chloride and 50 mL of ether, and extracted successively with 50 mL of saturated $NaHCO_3$, dithionite (25 mL, 10% aq.), and 20 mL of $NaHCO_3$. After each extraction, the resulting emulsion is broken by adding 20 mL of saturated NaCl solution to each extraction. The aqueous layer is decanted and the organic phase was dried over anhydrous $MgSO_4$. The solution is then filtered through a silica pad (3.1×7.5 cm) and washed with 50 mL of methylene chloride. Rotary evaporation and vacuum drying yields 22 g of crude product as a clear oil. The product is characterized by $^1H$ and $^{31}P$ NMR as a mixture of diasteromers. The reaction can be represented schematically as:

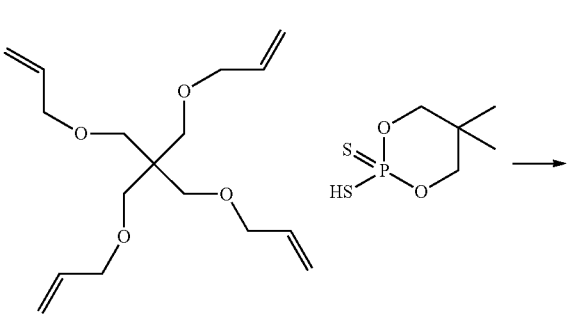

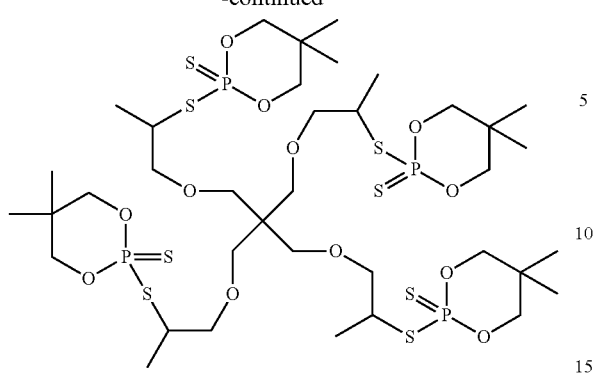

The 5% WLT for this product is 241° C. Plaques made from a blend of 4.6% of the product in 95.4% polystyrene have an LOI of 23.5 and an FP-7 value of 2.0 seconds.

Example 32

To a 500 mL three necked round bottom flask equipped with a stir shaft, a reflux condenser with nitrogen inlet and an addition funnel are added 76.96 g (0.388 mol) of 5,5-dimethyl-2-mercapto-1,3,2-dioxaphosphorinane 2-sulfide, 7 g (0.129 mol) of polybutadiene homopolymer dissolved in 60 mL of toluene and 140 mL of toluene. The polybutadience polymer contains 20% of 1,4-butadiene units and 80% of 1,2-butadiene units. The reaction mixture is immersed into an oil bath set to 85° C., and all solids dissolve in the toluene. The reaction mixture is allowed to heat and stir under nitrogen for 75 hours. The reaction solution is then cooled to 40° C. Triethylamine (37.35 mL, 0.268 mol) is added to the crude solution and the reaction mixture is then allowed to stir under nitrogen at 40° C. for 1 hour. A white precipitate forms. Toluene is removed from the crude mixture via rotary evaporation. THF (200 mL) is added directly to the white tacky solid and the mixture is allowed to stir at room temperature overnight. A white solid is filtered from the THF solution, and the filtrate is precipitated into 5 L of methanol. The white polymer precipitate is dried overnight under vacuum at 70° C., redissolved in 100 mL of THF, and re-precipitated into 2 L of methanol. The polymer is collected via filtration and dried overnight in a vacuum oven at 65° C. 26.85 g of white polymer powder is collected (82% yield).

$^1$H NMR in CDCl$_3$ shows 8.8% of the original carbon-carbon double bonds remain unreacted: δ 5.46 (vinyl), 5.18 (vinyl), 4.25 (2H, neopentyl), 3.97 (2H, neopentyl), 3.76 (1H), 3.50 (1H), 1.78 (—CH$_2$— backbone), 1.51 (—CH$_2$— backbone), 1.25 (3H, —CH$_3$), 0.97 (3H, —CH$_3$). $^{31}$P NMR (CDCl$_3$): s, 90.95 ppm The idealized reaction scheme is as follows:

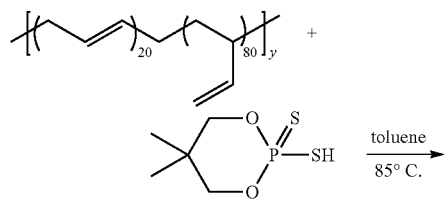

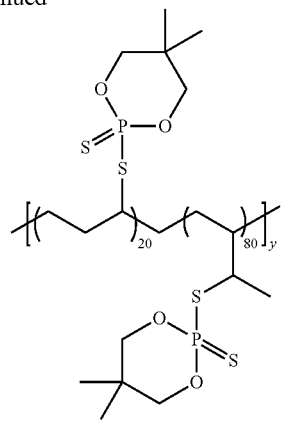

The 5% WLT for this product is 252° C. Plaques made from a blend of 4.6% of the product in 95.4% polystyrene have an LOI of 23 and an FP-7 value of 2.3 seconds.

Example 33

To a stirred solution of hexakis(bromomethyl)benzene (2.0 g, 3.2 mmol) and 5,5-dimethyl-2-thioxo-[1,3,2]dioxaphosphorinane-2-thiol (3.9 g, 19.8 mmol) in toluene (100 mL) is added triethylamine (2.0 g, 19.8 mmol). The mixture is heated to reflux for 6 hours and then cooled and filtered. A precipitate forms which is dissolved in methylene chloride (100 mL) and washed with saturated aqueous sodium bicarbonate solution (2×100 mL), dried over anhydrous magnesium sulfate and concentrated under reduced pressure to yield the 2,2',2'',2''',2'''',2'''''-[benzene-1,2,3,4,5,6-hexaylhexakis(methylenethio)]hexakis(5,5-dimethyl-1,3,2-dioxaphosphorinane) 2,2',2'',2''',2'''',2'''''-hexasulfide as a white solid (4.2 g, 99%). The proposed structure of the product is as follows:

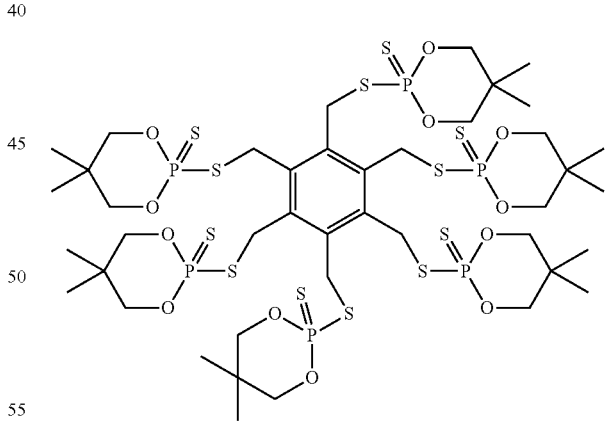

The 5% WLT for this material is 262° C. Plaques made from a blend of 5.3% of the product in 94.7% polystyrene have an LOI of 24.3 and an FP-7 value of 1.4 seconds.

Example 34

An unsaturated polyester is prepared from cyclohexanedimethanol (50/50 mixture of 1,4 and 1,3-isomer) and dimethyl fumarate. The weight average molecular weight of the unsaturated polyester (by GPC, relative to polystyrene) is 16,400 and its glass transition temperature ($T_g$) is 16° C. The unsaturated polyester (10.0 g) and anhydrous pyridine (2 ml) are dissolved in 30 ml methylene chloride, and to the solution is added acetic anhydride (3.0 g). After stirring under nitrogen for 24 hours, the polymer solution is washed with 30 mL of water, and the product is isolated by precipitation in methanol (250 mL). The product is dried 5 hours in a vacuum oven at 70° C. The resulting unsaturated polyester (5.0 g) and 5,5-dimethyl-2-mercapto-1,3,2-dioxaphosphorinane 2-sulfide (4.4 g, 22 mmol) are dissolved in 10 mL of 1,2-dichloroethane and the solution is refluxed for 23 hours. The solution is diluted by addition of 70 mL of 1,2-dichloroethane and the solution is washed with 30 ml of water that contains 1.0 g sodium bicarbonate. The product is isolated by precipitation in 500 mL of methanol. The product is dried overnight in a vacuum oven at 50° C. The weight average molecular weight of the product is 8800. Its $T_g$ is 45° C. 5% WLT for this product is 271° C. The idealized structure of the repeat units of the polymer are represented as:

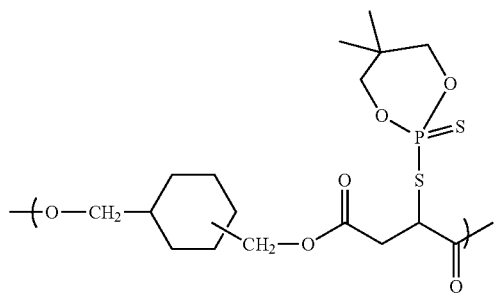

Plaques made from a blend of 10% of the product in 90% polystyrene have an LOI of 25.0 and an FP-7 value of 0.6 seconds.

Example 35

The allyl ether of m-cresol novolac is prepared from m-cresol novolac (weight average molecular weight of 1600) and allyl bromide. The m-cresol novolac (9.80 g) is dissolved in 70 mL N,N-dimethyl formamide (DMF), and sodium hydride (2.5 g) is added to the solution over 30 minutes. To this mixture is then added (over 30 minutes) allyl bromide (14.9 g). After stirring under nitrogen overnight, the reaction mixture is filtered, diluted with 70 mL toluene, and washed with 70 mL water. The resulting polymer solution is concentrated and dried overnight in a vacuum oven at 60° C., yielding 13.0 g of the allyl ether of m-cresol novolac with a weight average molecular weight of 1650. The allyl ether of m-cresol novolac (8.0 g) and 5,5-dimethyl-2-mercapto-1,3,2-dioxaphosphorinane 2-sulfide (14.8 g, 75 mmol) are dissolved in 10 mL toluene and heated at 100° C. The resulting mixture is diluted with 70 mL toluene and then washed with 50 mL water that contains 4 g sodium bicarbonate. The product os isolated by evaporating the toluene, and dried further overnight in a vacuum oven at 70° C. The weight average molecular weight of the product is 3100. Its $T_g$ is 450° C. 5% WLT for this product is 277° C. The idealized structure of the repeat units of the polymer are represented as:

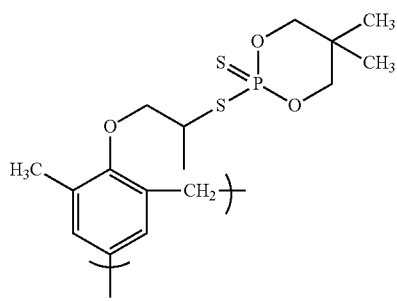

Plaques made from a blend of 9.4% of the product in 90.6% polystyrene have an LOI of 24.8 and an FP-7 value of 0.2 seconds.

Example 36

N,N'-methylene bisacrylamide (7.0 g, 0.045 mol) in 70 of tetrahydrofuran (THF) is added to a 250 mL three-necked round bottom flask equipped with magnetic stirring and a nitrogen inlet. 5,5-dimethyl-2-thioxo-[1,3,2]dioxaphosphorinane-2-thiol (18.0 g, 0.091 mole) is added and the resulting mixture is allowed to stir for 24 hours. The product is isolated by evaporation of THF, then recrystallized from 300 mL toluene. The resulting product is a crystalline white solid with melting point of 65° C. The idealized structure is as follows:

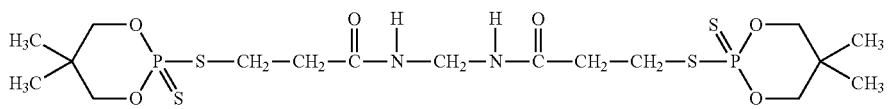

The 5% WLT for this material is 220° C. Plaques made from a blend of 6.9% of the product in 93.1% polystyrene have an LOI of 24.5 and an FP-7 value of 0.8 seconds.

Example 37

Triethylamine (2.02 g, 20 mmol) is added to a stirred solution of 1,3-bis(chloromethylphenyl)benzene (3.27 g, 10 mmol) and 5,5-dimethyl-1,3,2-dioxaphosphorinane-2-thiol (3.96 g, 20 mmol) in toluene (70 mL. The mixture is heated to reflux for 3 hours. The reaction mixture is cooled and washed with aqueous sodium bicarbonate solution (100 mL), dried and concentrated to yield 2,2'-{1,3-phenylenebis[(phenylmethylene)thio]}bis(5,5-dimethyl-1,3,2-dioxaphosphorinane)

2,2'-disulfide as a white solid. The yield of the product is 4.8 g (74%). The structure of the product is as follows:

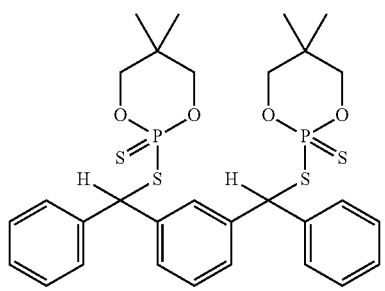

The 5% WLT for this material is 259° C. Plaques made from a blend of 8.1% of the product in 91.9% polystyrene have an LOI of 25.8% and an FP-7 value of 1 second.

Example 38

To a slurry of 2,4,8,10-tetraoxa-3,9-diphosphaspiro[5.5] undecane 3,9-disulfide (3 g, 11.5 mmol) in methylene chloride (50 mL) is added triethylamine (2.33 g, 23 mmol), followed by sulfur (0.74 g, 23 mmol) in portions. The mixture is allowed to stir for 1 hour at 40° C. Bromodiphenylmethane (5.7 g, 23 mmol) is added and the mixture is heated to 45° C. for 4 hours. The reaction mixture is worked up by washing with saturated sodium bicarbonate solution, drying over anhydrous $MgSO_4$ and concentrating under reduced pressure to yield 5.42 g (72%) of the product as white solid. The structure of the product is as follows:

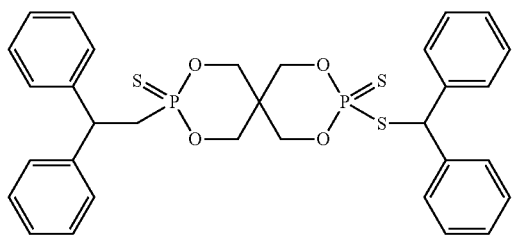

The 5% WLT for this material is 240° C. Plaques made from a blend of 8.2% of the product in 91.8% polystyrene have an LOI of 26.7% and an FP-7 value of 1.4 second.

What is claimed is:

1. A polymer composition comprising a combustible polymer and an effective amount of a phosphorus-sulfur additive represented by either of the structures:

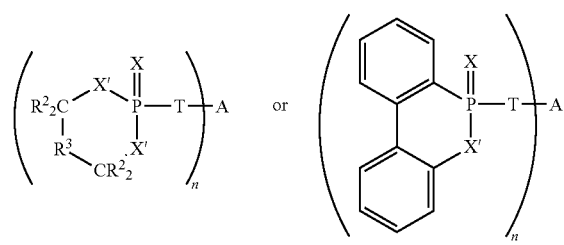

wherein X is oxygen or sulfur, T is sulfur or —$NR^4$—, wherein $R^4$ is hydrogen, alkyl or inertly substituted alkyl, provided that at least one of X and T is sulfur, each X' is independently oxygen or sulfur, n is at least 2, each $R^2$ is independently hydrogen, alkyl or inertly substituted alkyl, $R^3$ is a covalent bond or a divalent linking group and A is an organic linking group.

2. The polymer composition of claim 1 wherein the phosphorus-sulfur additive contains from 5 to 30% by weight of sulfur.

3. The polymer composition of claim 1 wherein T is sulfur, X is sulfur, each X' is oxygen, each $R^2$ is independently hydrogen or an alkyl group, and $R^3$ is a (dialkyl)methylene group.

4. The polymer composition of claim 1 wherein said phosphorus-sulfur additive is represented by the structure:

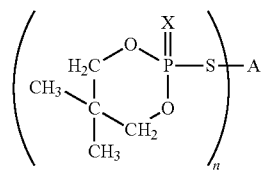

wherein X is oxygen or sulfur, A is an organic linking group, and n is at least 2.

5. The polymer composition of claim 1 wherein A is an organic polymer.

6. The composition of claim 2 wherein A is a polymer of styrene, a polymer of butadiene or a copolymer of styrene and butadiene.

7. The polymer composition of claim 1 wherein the combustible polymer is a polyolefin, a polycarbonate, a blend of polycarbonate with a polyester, a blend of a polycarbonate with an acrylonitrile-styrene-butadiene polymer, a blend of a polycarbonate and a styrene-acrylonitrile polymer, a blend of a polycarbonate and polystyrene, a polyamide, a polyester, an epoxy resin, a polyurethane, a vinyl aromatic polymer, a rubber-modified vinyl aromatic polymer, a styrene-acrylonitrile polymer, a styrene-butadiene copolymer or a mixture of two or more thereof.

8. The polymer composition of claim 7 wherein the combustible polymer is a foam.

9. A phosphorus-sulfur compound represented by the structure:

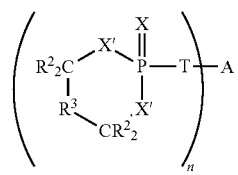

wherein X is oxygen or sulfur, T sulfur or —$NR^4$—, wherein $R^4$ is hydrogen, alkyl or inertly substituted alkyl, provided that at least one of X and T is sulfur, each X' is independently oxygen or sulfur, n is at least 2, each $R^2$ is independently hydrogen, alkyl or inertly substituted alkyl, $R^3$ is a covalent bond or a divalent linking group and A is an organic linking group.

10. The phosphorus-sulfur compound of claim 9 wherein each X' is oxygen, T is sulfur, X is sulfur, each $R^2$ is hydrogen, and $R^3$ is an alkylene diradical having no hydrogens on the carbon atom(s) bonded directly to the adjacent $(R^2)_2C$ groups.

11. The phosphorus-sulfur compound of claim 10 wherein the A group is an organic polymer.

12. A phosphorus-sulfur compound represented by the structure:

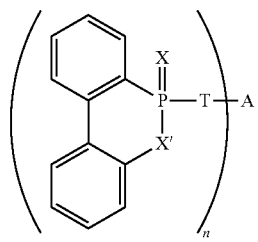

wherein X is oxygen or sulfur, T is sulfur or —NR$^4$—, wherein R$^4$ is hydrogen, alkyl or inertly substituted alkyl, provided that at least one of X and T is sulfur, X' is oxygen or sulfur, n is at least 2 and A is an organic linking group.

13. The phosphorus-sulfur compound of claim 12 wherein the A group is an organic polymer.

* * * * *